US011913925B2

(12) United States Patent
Lo et al.

(10) Patent No.: US 11,913,925 B2
(45) Date of Patent: Feb. 27, 2024

(54) SENSING DEVICES AND CALIBRATION METHOD THEREOF

(71) Applicant: Industrial Technology Research Institute, Hsinchu (TW)

(72) Inventors: Ying-Che Lo, Tainan (TW); Yu-Sheng Lin, Tainan (TW); Po-Jen Su, Tainan (TW); Ting-Hao Hsiao, Chiayi County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 181 days.

(21) Appl. No.: 17/125,968

(22) Filed: Dec. 17, 2020

(65) Prior Publication Data
US 2022/0074903 A1    Mar. 10, 2022

(30) Foreign Application Priority Data

Sep. 10, 2020   (TW) .................................. 109131091

(51) Int. Cl.
*G01L 27/00*   (2006.01)
*G01L 9/12*    (2006.01)
(Continued)

(52) U.S. Cl.
CPC ........... *G01N 33/0006* (2013.01); *G01K 7/16* (2013.01); *G01L 9/125* (2013.01); *G01L 27/002* (2013.01); *G01N 27/121* (2013.01)

(58) Field of Classification Search
CPC ........... G01N 33/0004; G01N 33/0006; G01N 27/121; G01N 27/122; G01N 27/123;
(Continued)

(56) References Cited

U.S. PATENT DOCUMENTS 5,848,383 A    12/1998 Yunus
7,373,266 B2    5/2008 Petersen et al.
(Continued)

FOREIGN PATENT DOCUMENTS

CN    201510284 U    6/2010
CN    101344535 B    9/2010
(Continued)

OTHER PUBLICATIONS

Taiwan Patent Office, Office Action, Patent Application Serial No. 109131091, dated Jun. 9, 2021, Taiwan
(Continued)

*Primary Examiner* — Herbert K Roberts

(57) ABSTRACT

A sensing device is provided. The sensing device includes a processing circuit and a multi-sensor integrated single chip. The multi-sensor integrated single chip includes a substrate and a temperature sensor, a pressure sensor, and an environmental sensor disposed on the substrate. The temperature sensor senses temperature. The pressure sensor senses pressure. The environmental sensor senses an environmental state. The processing circuit obtains a first sensed temperature value from the temperature sensor when the environmental sensor does not operate, and it obtains a second sensed temperature value from the temperature sensor when the environmental sensor operates. The processing circuit obtains a sensed pressure value from the pressure sensor. The processing circuit obtains at least one temperature calibration reference of the pressure sensor according to the first and second sensed temperature values and calibrates the sensed pressure value according to the temperature calibration reference.

24 Claims, 16 Drawing Sheets

(51) Int. Cl.
    *G01N 33/00* (2006.01)
    *G01N 27/12* (2006.01)
    *G01K 7/16* (2006.01)

(58) Field of Classification Search
    CPC ........ G01N 27/124; G01K 7/16; G01L 9/125;
        G01L 27/002; G01L 27/005
    See application file for complete search history.

(56) References Cited

U.S. PATENT DOCUMENTS

| | | | |
|---|---|---|---|
| 7,520,170 | B2 | 4/2009 | Murayama |
| 7,577,539 | B2 | 8/2009 | Hubanks et al. |
| 8,186,226 | B2 | 5/2012 | Ricks |
| 8,397,571 | B2 | 3/2013 | Murayama |
| 8,453,501 | B2 | 6/2013 | Kimura |
| 9,927,266 | B2 | 3/2018 | Dawson et al. |
| 2014/0190237 | A1* | 7/2014 | Park .................. G01L 27/00 73/1.57 |
| 2017/0122783 | A1 | 5/2017 | Xue et al. |
| 2019/0033274 | A1* | 1/2019 | Makaram ........... G01N 33/0008 |
| 2019/0086284 | A1 | 3/2019 | Macneil et al. |
| 2019/0145834 | A1* | 5/2019 | Nakamura ............... G01K 7/16 374/164 |
| 2019/0310212 | A1* | 10/2019 | Ando ..................... G01N 25/56 |

FOREIGN PATENT DOCUMENTS

| | | | | | |
|---|---|---|---|---|---|
| CN | 101776596 | B | 8/2011 | | |
| CN | 202110029 | U | 1/2012 | | |
| CN | 101858930 | B | 4/2013 | | |
| CN | 204422133 | U | 6/2015 | | |
| CN | 104914275 | A | 9/2015 | | |
| CN | 106771361 | A | 5/2017 | | |
| CN | 111579619 | A | 8/2020 | | |
| EP | 2827145 | A1 * | 1/2015 | ......... | G01N 33/0008 |
| JP | 2018048963 | A * | 3/2018 | .............. | G01D 1/16 |
| TW | 341000 | B | 9/1998 | | |
| TW | 1407700 | B | 9/2013 | | |
| TW | 1506246 | B | 11/2015 | | |
| TW | 1588726 | B | 6/2017 | | |

OTHER PUBLICATIONS

Mason, Andrew, et al., "A Mixed-Voltage Sensor Readout Circuit With On-Chip Calibration and Built-In Self-Test", IEEE Sensors Journal, Sep. 2007, pp. 1225-1232, Vol. 7, No. 9, IEEE, US.

Maenaka, Kazusuke, et al., "Application of Multi-Environmental Sensing System in MEMS Technology", Int. Conf. on Networked Sensing Systems, 2007, 6 pages.

Fujita, Takayuki, et al., "SOI-MEMS Sensor for Multi-Environmental Sensing-System", Proc. of The 4th Int. Conf. on Networked Sensing Systems, 2007, 4 pages.

Clifford, Mark. "Ultra-Low Power Pressure Sensing A Capacitive Based MEMS Approach", Proc. of Sensor and Test Conf., 2009. pp. 187-192.

Mathieu, Hautefeuille, et al. "Development of a Microelectromechanical System (MEMS)-Based Multisensor Platform for Environmental Monitoring", Micromachines, 2011, 22 pages.

Leo, Chemmanda John, et al., "A Fully Integrated Capacitance Boosting Offset Calibration Circuit for Capacitive Pressure Sensor", Proc. Int. Symp. Integrated Circuits, 2016, 5 pages, IEEE, US.

Xue, Ning, et al., "Highly Integrated MEMS-ASIC Sensing System for Intracorporeal Physiological Condition Monitoring", Sensors, 2018, 15 pages, MDPI, US.

* cited by examiner

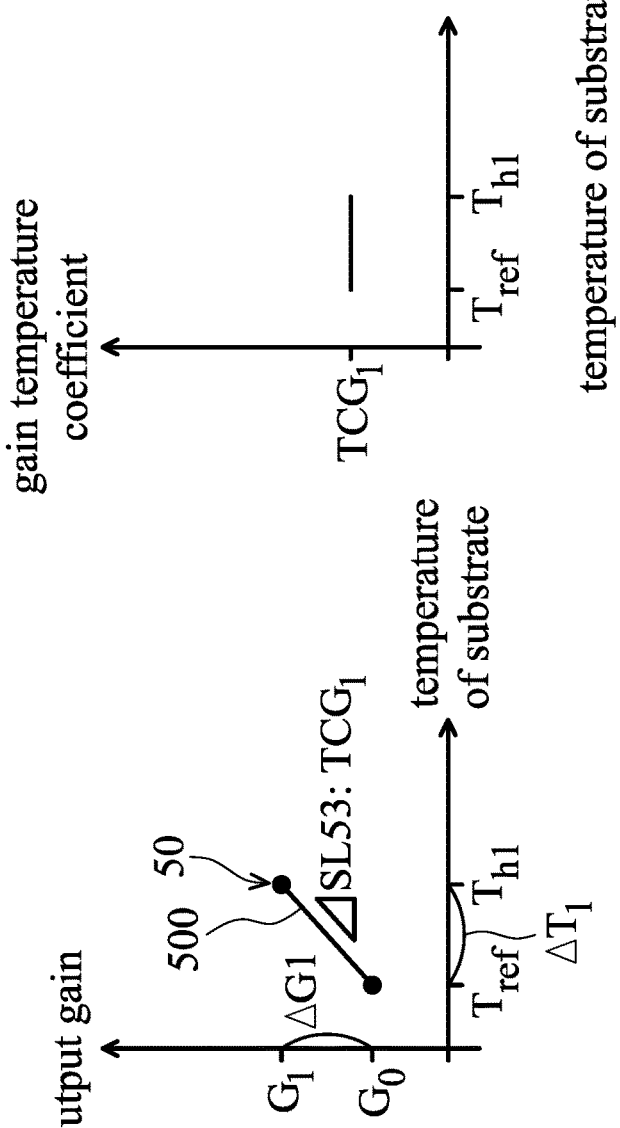
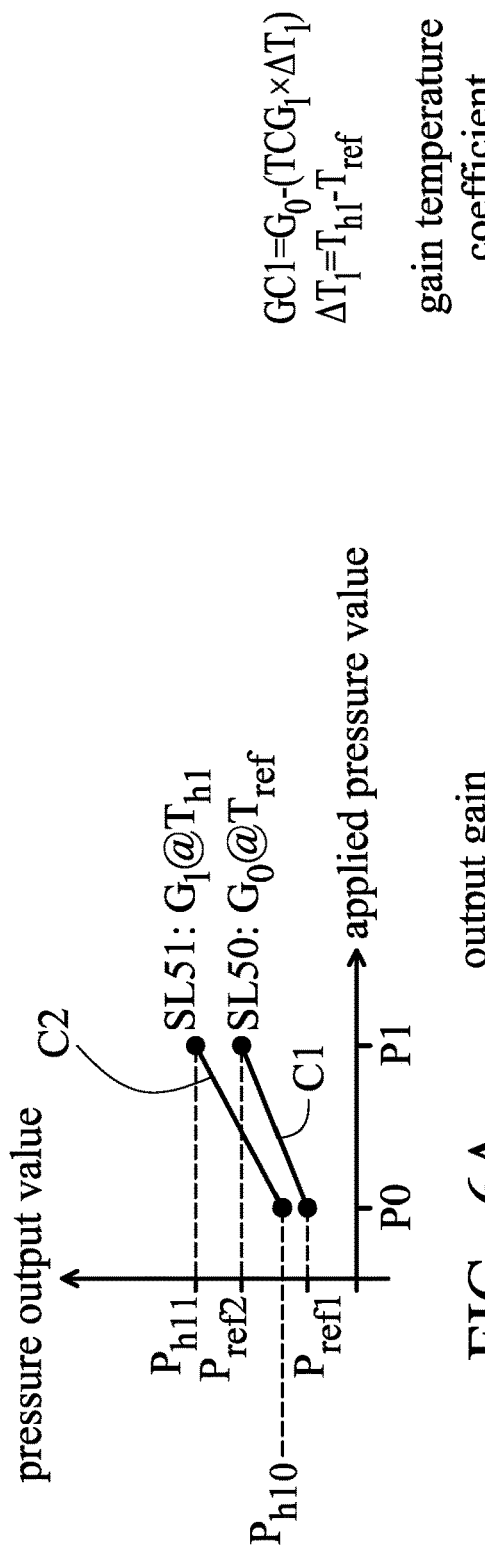
FIG. 6A
FIG. 6B
FIG. 6C

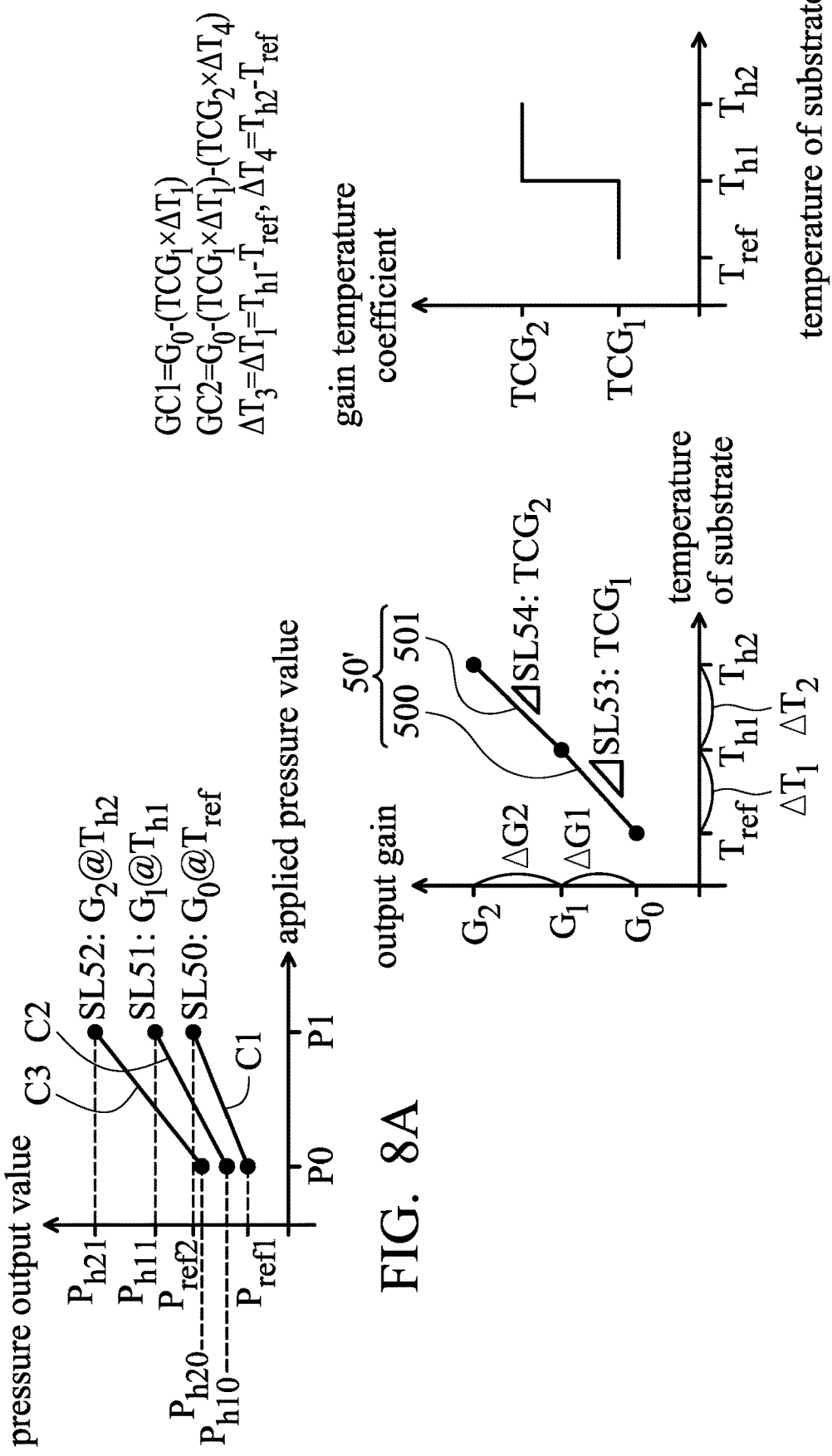

SENSING DEVICES AND CALIBRATION METHOD THEREOF

CROSS REFERENCE TO RELATED APPLICATIONS

This application claims priority of Taiwan Patent Application No. 109131091, filed on Sep. 10, 2020, the entirety of which is incorporated by reference herein.

BACKGROUND

Field of the Invention

The present disclosure relates to a sensing device, and more particularly to a sensing device with a multi-sensor integrated on single chip and a calibration method thereof.

Description of the Related Art

Recently, environmental sensing technologies are developing toward multi-function, miniaturization, and low prices to make them popular. In existing conventional multi-function sensing device, the sensors may interfere with each other, affecting sensing accuracy. For example, in a sensing device which combines a gas sensor and a pressure sensor, when the gas sensor is operating, the heater of the gas sensor is activated at the same time and causes a rise in temperature. Since the pressure sensor relates to a temperature coefficient, the rise in temperature leads to the output voltage offset and gain drift of the pressure sensor. However, conventional sensing devices which combine a gas sensor and a pressure sensor lack a calibration mechanism for the pressure sensor. When the impact of the above-mentioned temperature rise becomes serious, the output voltage of the pressure sensor will saturate, and the pressure sensor will not work correctly. Therefore, eliminating interference between sensors is important to the multi-function sensing device.

SUMMARY

According to an embodiment of the present disclosure, a sensing device comprises a processing circuit and a multi-sensor integrated single chip. The multi-sensor integrated single chip is electrically connected to the processing circuit. The multi-sensor integrated single chip comprises a substrate, a temperature sensor, a pressure sensor, and a first environmental sensor. The temperature sensor is disposed on the substrate and configured to sense temperature. The pressure sensor is disposed on the substrate and configured to sense pressure. The first environmental sensor is disposed on the substrate and configured to sense a first environmental state. The processing circuit is configured to: obtain a first sensed temperature value from the temperature sensor when the first environmental sensor does not operate; obtain a second sensed temperature value from the temperature sensor when the first environmental sensor operates; obtain a sensed pressure value from the pressure sensor; and obtain at least one temperature calibration parameter of the pressure sensor according to the first sensed temperature value and the second sensed temperature value and calibrate the sensed pressure value according to the at least one temperature calibration parameter to generate a calibrated pressure value.

According to an embodiment of the present disclosure, a sensing device comprises a multi-sensor integrated single chip and a processing circuit. The multi-sensor integrated single chip comprises a temperature sensor, a pressure sensor, and a first environmental sensor. The calibration method for a sensing device comprises the following steps: by the processing circuit, driving the temperature sensor to sense temperature and generating a first sensed temperature value; by the processing circuit, driving the first environmental sensor to operate, and driving the temperature sensor to sense temperature to operate, and generating a second sensed temperature value; by the processing circuit, driving the pressure sensor to sense pressure and generating a sensed pressure value; and by the processing circuit, obtaining at least one temperature calibration parameter of the pressure sensor according to the first sensed temperature value and the second sensed temperature value and correcting the sensed pressure value according to the at least one temperature calibration parameter to generate a calibrated pressure value.

A detailed description is given in the following embodiments with reference to the accompanying drawings.

BRIEF DESCRIPTION OF THE DRAWINGS

FIGS. 4B-1 and 4B-2 show a flowchart of a method for generating temperature calibration parameters according to another embodiment of the present disclosure;

FIG. 6A shows pressure change curves at respective sensed temperature values when the atmospheric pressure changes according to one embodiment of the present disclosure;

FIG. 6B shows a curve depicting the relationship between different sensed temperature values and corresponding output gains according to one embodiment of the present disclosure;

FIG. 6C is a schematic diagram showing relationship between the sensed temperature values and a gain temperature coefficient according to one embodiment of the present disclosure;

FIG. 8A shows pressure change curves at respective sensed temperature values when the atmospheric pressure changes according to another embodiment of the present disclosure;

FIG. 8B shows a curve depicting the relationship between different sensed temperature values and corresponding output gains according to another embodiment of the present disclosure;

FIG. 8C is a schematic diagram showing relationship between the sensed temperature values and corresponding gain temperature coefficients according to another embodiment of the present disclosure;

DETAILED DESCRIPTION

The following description is of the best-contemplated mode of carrying out the invention. This description is made for illustrating the general principles of the invention and should not be taken in a limiting sense. The scope of the invention is best determined by reference to the appended claims.

Figure 1A:
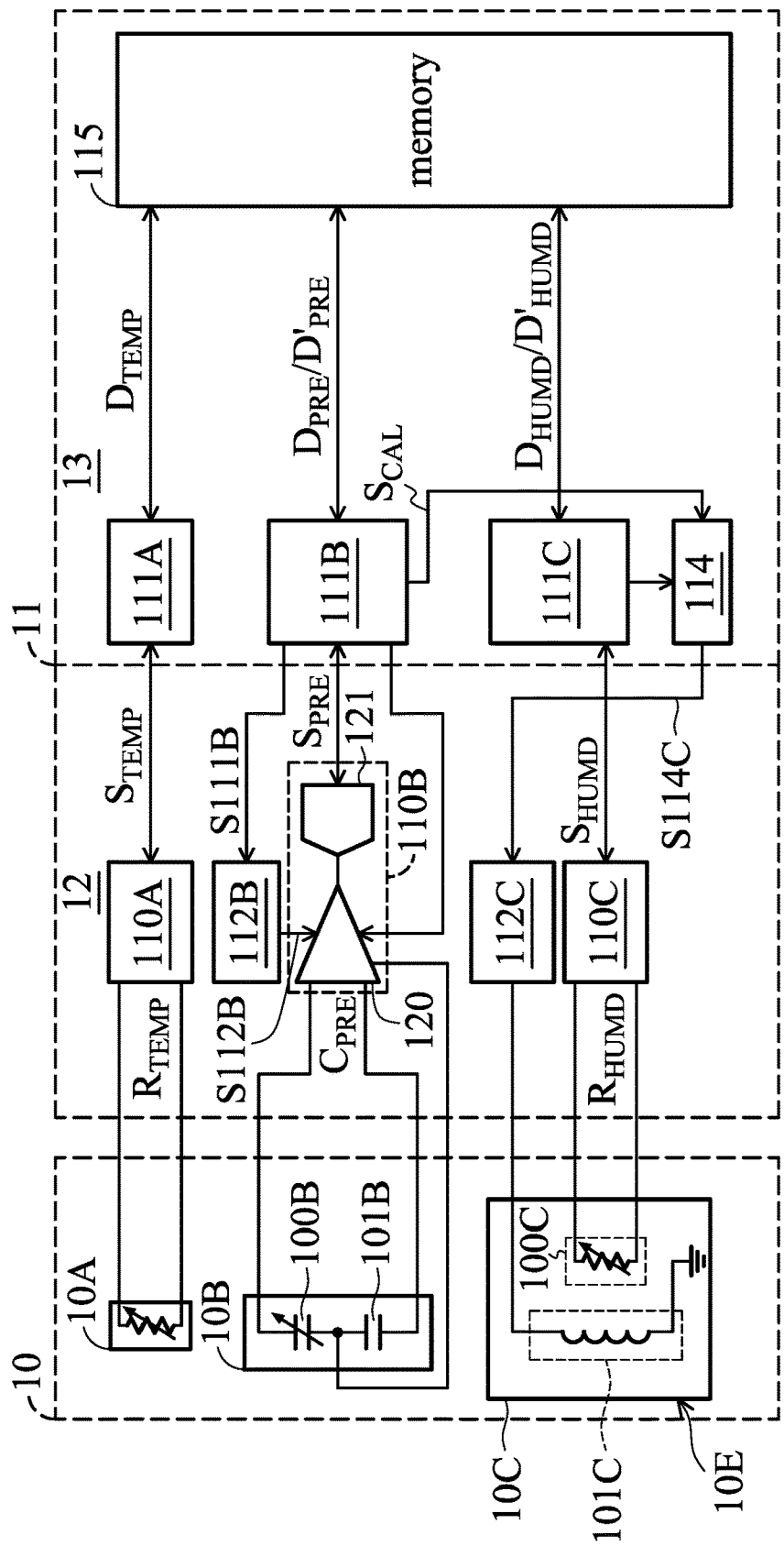
FIG. 1A shows a sensing device according to one embodiment of the present disclosure.

FIG. 1A shows a sensing device according to one embodiment of the present disclosure. Referring to FIG. 1A, a sensing device 1 comprises a processing circuit 11 and a multi-sensor integrated single chip 10 electrically connected to the processing circuit 11. The multi-sensor integrated single chip 10 comprises a substrate (not shown), a temperature sensor 10A, a pressure sensor 10B, and a first environmental sensor 10E. The temperature sensor 10A, the pressure sensor 10B, and the first environmental sensor 10E are disposed on the same substrate (not shown). The temperature sensor 10A operates to sense temperature, the pressure sensor 10B operates to sense pressure, and the first environmental sensor 10E operates to sense a first environmental state. In the embodiment shown in FIG. 1A, the first environmental sensor 10E is a humidity sensor 10C, and the first environmental state is relative humidity.

Figure 1B:
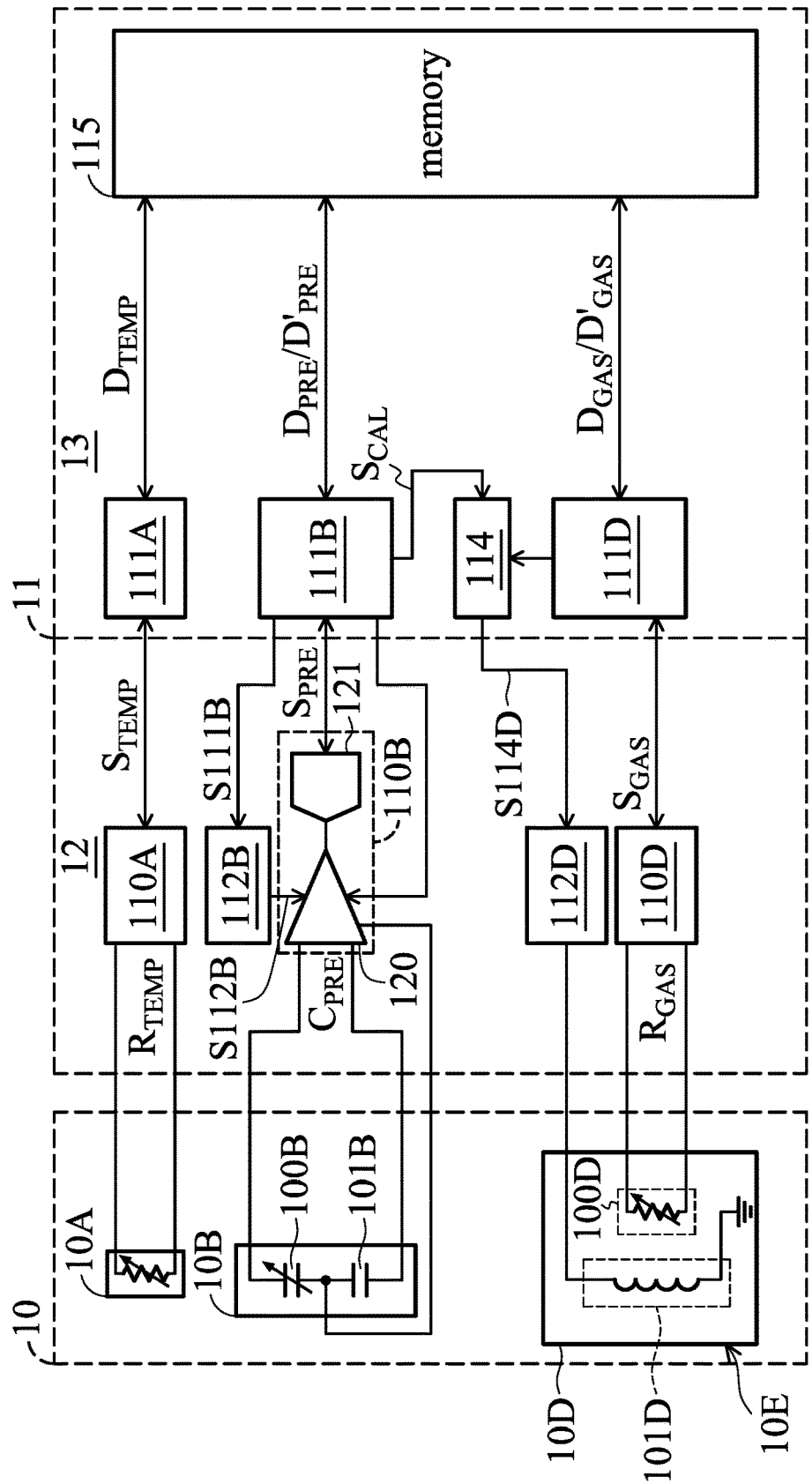
FIG. 1B shows a sensing device according to another embodiment of the present disclosure.

FIG. 1B shows a sensing device according to another embodiment of the present disclosure. Referring to FIG. 1B, the sensing device 1 of the embodiment is similar to the embodiment shown in FIG. 1A. The difference between the embodiment shown in FIG. 1B and the embodiment shown in FIG. 1A is that the first environmental sensor 10E of the embodiment is a gas sensor 10D, and the first environmental state of the embodiment is gas concentration.

Figure 3A:
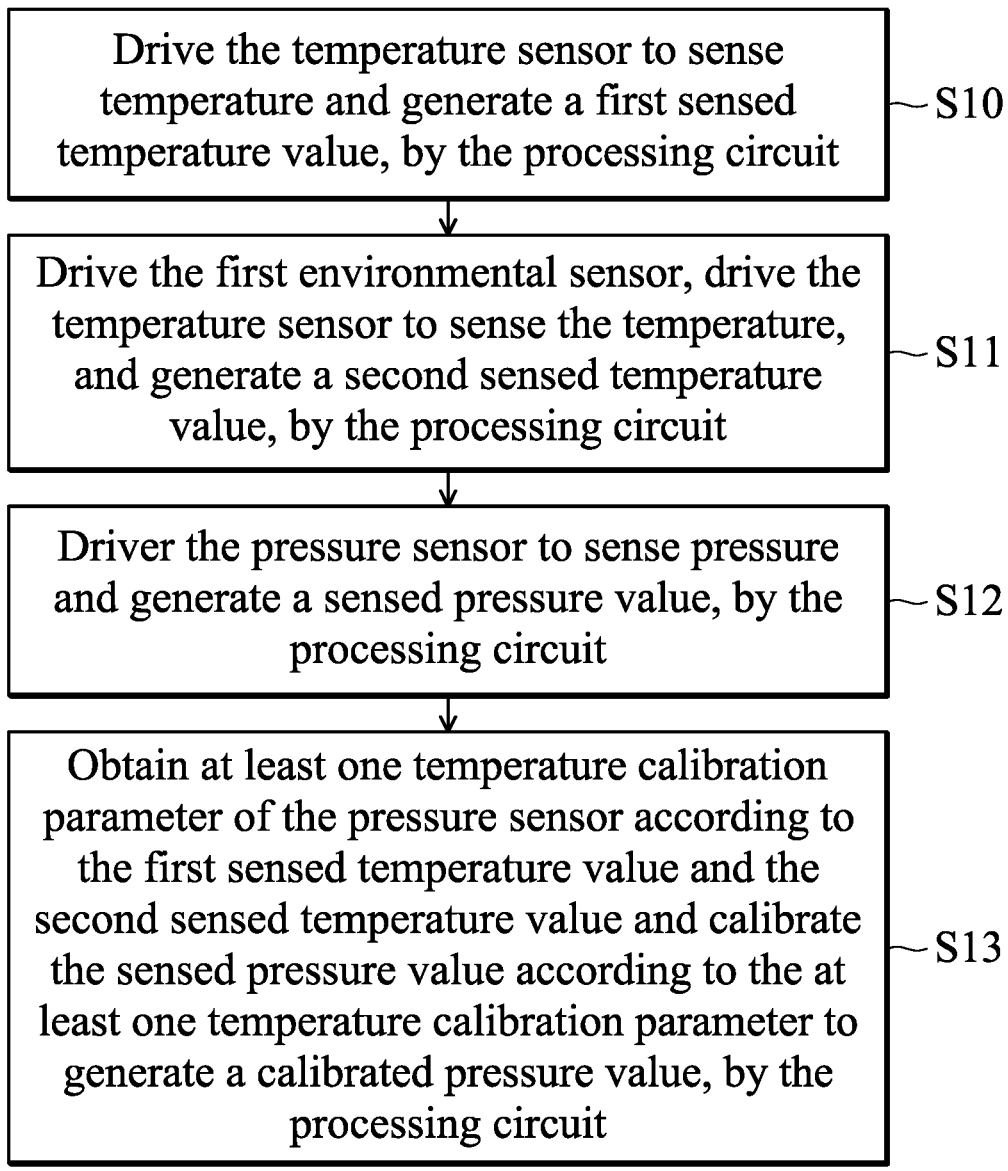
FIG. 3A is a flowchart of a calibration method according to one embodiment of the present disclosure.

FIG. 3A is a flowchart of a calibration method according to one embodiment of the present disclosure. Referring to FIG. 3A, a calibration method is applicable to the sensing device 1 shown in FIG. 1A or FIG. 1B. The steps of the calibration method are described in the following. Step S10 is performed. In Step S10, the processing circuit 11 drives the temperature sensor 10A to sense temperature and generates a first sensed temperature value. Step S11 is then performed. In Step S11, the processing circuit 11 drives the first environmental sensor 10E to operate, drives the temperature sensor 10A to sense temperature, and generates a second sensed temperature value. Step S12 is performed. In Step S12, the processing circuit 11 drives the pressure sensor 10B to sense pressure and generates a sensed pressure value. Then, Step S13 is performed. In Step S13, the processing circuit 11 obtains at least one temperature calibration parameter of the pressure sensor 10B according to the first sensed temperature value and the second sensed temperature value and calibrates the sensed temperature value according to the at least one temperature calibration parameter to generate a calibrated pressure value.

Figure 1C:
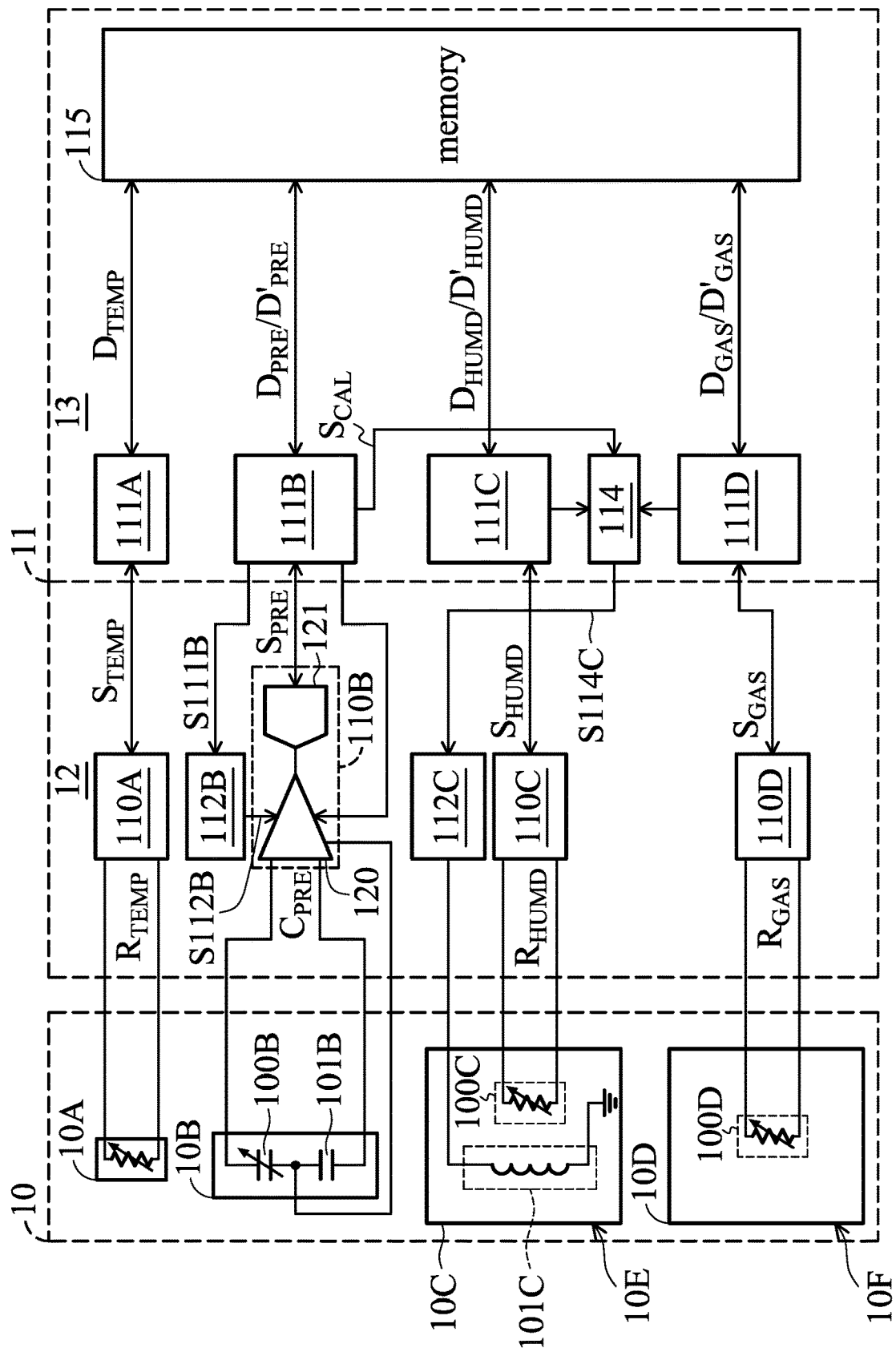
FIG. 1C shows a sensing device according to another embodiment of the present disclosure.
Figure 2:
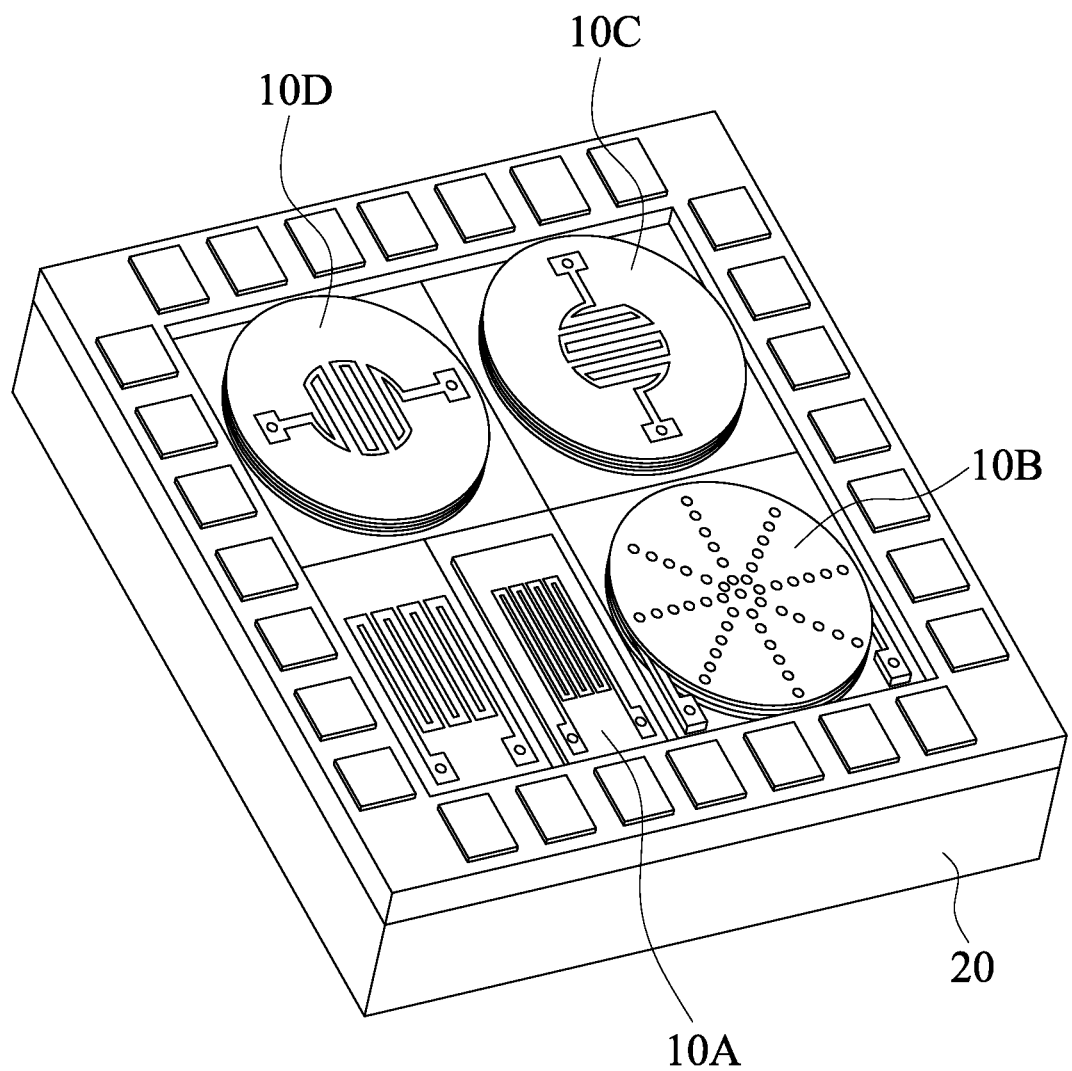
FIG. 2 is a schematic diagram showing a multi-sensor integrated single chip of the sensing device of FIG. 1C according to an embodiment of the present disclosure.

FIG. 1C shows a sensing device according to another embodiment of the present disclosure, and FIG. 2 is a schematic diagram of the sensing device. Referring to FIGS. 1C and 2, the sensing device 1 comprises a processing circuit 11 and a multi-sensor integrated single chip 10 electrically connected to the processing circuit 11. The multi-sensor integrated single chip 10 comprises a substrate 20, a temperature sensor 10A, a pressure sensor 10B, a first environmental sensor 10E, and a second environmental sensor 10F. The temperature sensor 10A, the pressure sensor 10B, the first environmental sensor 10E, and the second environmental sensor 10F are arranged on the same substrate 20. The temperature sensor 10A operates to sense temperature, and the pressure sensor 10B operates to sense pressure. The first environmental sensor 10E operates to sense a first environmental state, and the second environmental sensor 10F operates to sense a second environmental state. In the embodiment, the first environmental sensor 10E is a humidity sensor 10C, and the first environmental state is relative humidity. The second environmental sensor 10F is a gas sensor 10D, and the second environmental state is gas concentration.

The temperature sensor 10A is a resistive sensor, that is, the resistance value of the resistive sensor reflects the environmental temperature. The pressure sensor 10B comprises a pressure sensing element 100B and a reference capacitor 10E. The pressure sensor 10B of the embodiment is a capacitive sensor, which reflects the environmental pressure through the capacitance value. However, in other embodiments, the pressure sensor 10B may also be a resistive sensor which reflects the environmental pressure through the resistance value. The humidity sensor 10C comprises a first sensing element 100C and a first heater 101C. The humidity sensor 10C is a resistive sensor which reflects the relative humidity of the environment through the resistance value. The gas sensor 10D comprises a second sensing element 100D. The gas sensor 10D of the embodiment is a resistive sensor which reflects the gas concentration of the environment through the resistance value.

The processing circuit 11 comprises a reading and calibration unit 12 and a digital control unit 13. The reading and calibration unit 12 comprises a temperature reading circuit 110A, a pressure reading circuit 110B, a pressure calibration circuit 112B, a humidity reading circuit 110C, a first heating driving circuit 112C, and a gas-concentration reading circuit 110D. The pressure reading circuit 110B comprises an analog front-end circuit 120 and a delta-sigma modulated analog-to-digital converter 121. The digital control unit 13 comprises a temperature calculation circuit 111A, a pressure calculation circuit 111B, a humidity calculation circuit 111C, a gas-concentration calculation circuit 111D, a heating control circuit 114, and a memory 115 capable of storing data. The processing circuit 11 may be integrated on the same chip to form an application specific integrated circuit (ASIC) or implemented by using a field programmable gate array (FPGA). However, in other embodiments, the processing circuit 11 and the reading and calibration unit 12 may be integrated into the same chip, and the digital control unit 13 is integrated on another chip.

Figure 3B:
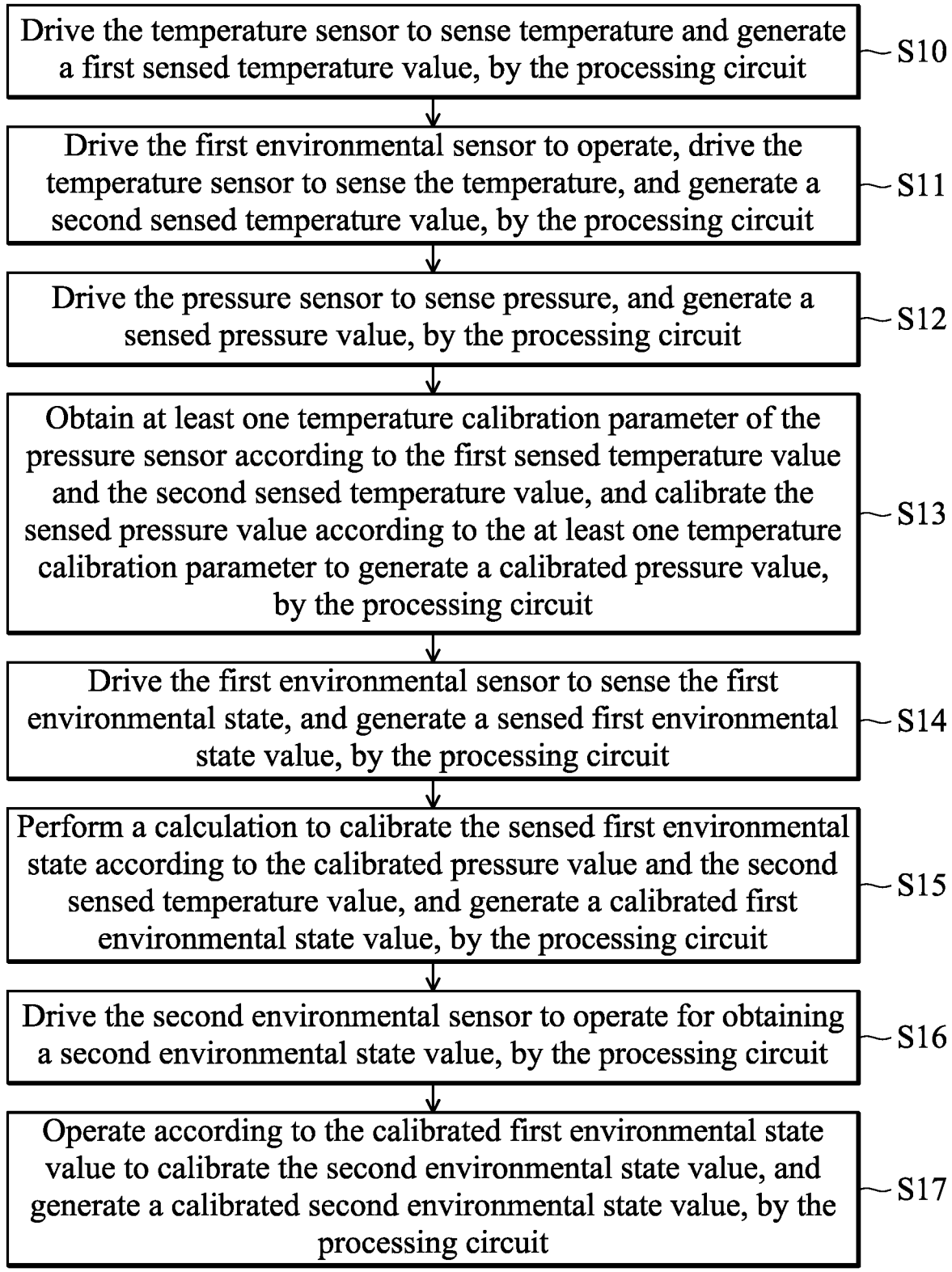
FIG. 3B is a flowchart of a calibration method according to another embodiment of the present disclosure.

FIG. 3B is a flowchart of a calibration method according to another embodiment of the present disclosure. Referring to FIG. 3B, the calibration method is applicable to the sensing device 1 shown in FIG. 1C. The steps of the calibration method are described in the following. Step S10 is performed. In Step S10, the processing circuit 11 drives the temperature sensor 10A to sense temperature and generates a first sensed temperature value. Step S11 is then performed. In Step S11, the processing circuit 11 drives the first environmental sensor 10E to operate, drives the temperature sensor 10A to sense the temperature, and generates a second sensed temperature value. Step S12 is performed. In Step S12, the processing circuit 11 drivers the pressure sensor 10B to sense pressure and generates a sensed pressure value. Then, Step S13 is performed. In Step S13, the processing circuit 11 obtains at least one temperature calibration parameter of the pressure sensor 10B according to the first sensed temperature value and the second sensed temperature value and calibrates the sensed pressure value according to the at least one temperature calibration parameter to generate a calibrated pressure value.

Then, Step S14 is performed. In Step S14, the processing circuit 11 drives the first environmental sensor 10E to sense the first environmental state and generates a sensed first environmental state value. In Step S15, the processing circuit 11 performs a calculation to calibrate the sensed first environmental state according to the calibrated pressure value and the second sensed temperature value and generates a calibrated first environmental state value. Step S16 is then performed. In Step S16, the processing circuit 11 drives the second environmental sensor 10F for obtaining a second environmental state value. Step S17 is performed. In Step S17, the processing circuit 11 operates according to the calibrated first environmental state value to calibrate the second environmental state value and generates a calibrated second environmental state value. In the embodiment, the first environmental sensor 10E is a humidity sensor 10C, and the first environmental state value is a relative humidity value; the second environmental sensor 10F is a gas sensor 10D, and the second environmental state value is a gas-concentration value. The operation details of the calibration method of the embodiment will be described in the following.

The resistance value of the temperature sensor 10A varies with the environmental temperature or the temperature of the substrate 20, and it is referred to herein as the temperature sensing resistance value $R_{TEMP}$. When the sensing device 1 senses the environmental temperature, the temperature reading circuit 110A can obtain the temperature sensing resistance value $R_{TEMP}$ and convert the temperature sensing resistance value $R_{TEMP}$ into a digital temperature signal $S_{TEMP}$. The temperature calculation circuit 111A may control the temperature reading circuit 110A. The temperature calculation circuit 111A is configured to receive and process the digital temperature signal $S_{TEMP}$ and generate the sensed temperature value $D_{TEMP}$ corresponding to the digital temperature signal $S_{TEMP}$ according to an environmental temperature look-up table stored in the memory 115. The sensed temperature value $D_{TEMP}$ reflects the current environmental temperature. The temperature calculation circuit 111A is also configured to store the sensed temperature value $D_{TEMP}$ in the memory 115.

The capacitance value of the pressure sensing element 100B of the pressure sensor 10B varies with environmental pressure. For example, the environmental pressure is reflected in the variation of the capacitance between the two terminals of the circuit composed of the pressure sensing element 100B and the reference capacitor 101B, and the capacitance therebetween is referred to herein as the pressure sensing capacitance $C_{PRE}$. When the sensing device 1 operates to sense the environmental pressure, the pressure reading circuit 110B obtains the pressure sensing capacitance $C_{PRE}$, and the analog front-end circuit 120 and the delta-sigma modulated analog-to-digital converter 121 of the pressure reading circuit 110B perform a conversion on the pressure sensing capacitance $C_{PRE}$ and generate a digital pressure signal $S_{PRE}$ corresponding to the capacitance value. The pressure calculation circuit 111B may control the operation of the analog front-end circuit 120. The pressure calculation circuit 111B is configured to receive and process the digital pressure signal $S_{PRE}$ and generate a sensed pressure value $D_{PRE}$ corresponding to the digital pressure signal $S_{PRE}$ according to an environmental pressure look-up table stored in the memory 115. The sensed pressure value $D_{PRE}$ reflects the current environmental pressure. The pressure calculation circuit 111B is also configured to store the sensed pressure value $D_{PRE}$ in the memory 115. The pressure calibration circuit 112B is coupled to the analog front-end circuit 120 and used to calibrate the digital pressure signal $S_{PRE}$. In an embodiment, the pressure calibration circuit 112B performs the calibration according to at least one temperature calibration parameter, such as an output offset calibration parameter or an output gain calibration parameter.

The pressure calculation circuit 111B reads the sensed temperature value $D_{TEMP}$, which was obtained when the sensing of the environmental pressure was performed previously, from the memory 115 and obtains at least one temperature calibration parameter according to the sensed temperature value $D_{TEMP}$ which is read out from the memory 115. The pressure calculation circuit 111B generates a control signal S111B according to the at least one obtained temperature calibration parameter and provides the control signal S111B to the pressure calibration circuit 112B. In the process of converting the pressure sensing capacitance $C_{PRE}$ into a digital pressure signal $S_{PRE}$, the analog front-end circuit 120 adjusts the output offset and output gain of the analog front-end circuit 120 according to the received temperature calibration parameter(s), thereby effecting a calibration of the drift of the output offset and output gain with the temperature. After temperature calibration, the pressure calculation circuit 111B generates the calibrated pressure value $D'_{PRE}$ and stores the calibrated pressure value $D'_{PRE}$ in the memory 115. The content related to the generation of the temperature calibration parameter(s) and the temperature calibration for the output offset and output gain will be described later.

During the process of sensing the humidity performed by the humidity sensor 10C of the embodiment, the heating control circuit 114 generates a signal S114C to control the first heating driving circuit 112C to output a voltage which is provided to drive the first heater 101C. In response to the voltage, the first heater 101C generates thermal energy to heat the first sensing element 100C and the substrate 20, that is, to raise the environmental temperature. The resistance value of the first sensing element 100C of the humidity sensor 10C changes with the environmental humidity. For example, the environmental humidity is reflected in the resistance value between the two terminals of the first sensing element 100C, and the resistance value therebetween is referred to herein as the humidity sensing resistance value $R_{HUMD}$. When the sensing device 1 operates to sense the environmental humidity, the humidity reading circuit 110C obtains the humidity sensing resistance value $R_{HUMD}$ and converts the humidity sensing resistance value $R_{HUMD}$ into a digital humidity signal $S_{HUMD}$ corresponding to the resistance value. The humidity calculation circuit 111C may control the humidity reading circuit 110C. The humidity calculation circuit 111C is further configured to receive and process the digital humidity signal $S_{HUMD}$ and generate the relative humidity value $D_{HUMD}$ corresponding to the digital humidity signal $S_{HUMD}$ according to a relative humidity look-up table stored in the memory 115. The humidity calculation circuit 111C reads the sensed temperature value $D_{TEMP}$, which was obtained when the sensing of the environmental humidity was performed, and the calibrated pressure value $D'_{PRE}$, which was generated in response to the temperature calibration operation, from the memory 115 and further calibrates the relative humidity value $D_{HUMD}$ according to the sensed temperature value $D_{TEMP}$ and the calibrated pressure value $D'_{PRE}$ to generate a calibrated humidity value $D'_{HUMD}$. The calibrated humidity value $D'_{HUMD}$ may more accurately reflect the actual relative humidity of the environment. The humidity calculation circuit 111C stores the calibrated humidity value $D'_{HUMD}$ in the memory 115.

In the process of sensing the gas concentration performed by the gas sensor 10D of the embodiment, the heating control circuit 114 generates the signal S114C to control the first heating driving circuit 112C to output a voltage which is provided to drive the first heater 101C. In response to the voltage, the first heater 101C generates thermal energy to heat the substrate 20 and further raise the temperature of the second sensing element 100D. The resistance value of the second sensing element 100D of the gas sensor 10D varies with the gas concentration of the environment. For example, the gas concentration is reflected in the resistance value between the two terminals of the second sensing element 100D, and the resistance value is referred to herein as a gas sensing resistance value $R_{GAS}$. When the sensing device 1 operates to sense the gas concentration of the environment, the gas-concentration reading circuit 110D obtains the gas sensing resistance value $R_{GAS}$ and converts the gas sensing resistance value $R_{GAS}$ into a digital gas signal $S_{GAS}$. The gas-concentration calculation circuit 111D performs a gas-concentration calculation using the digital gas signal $S_{GAS}$ and a baseline resistance value of the gas sensor 10D which is stored in the memory 115 to obtain a gas-concentration value $D_{GAS}$. The gas-concentration calculation circuit 111D reads, from the memory 115, the sensed temperature value $D_{TEMP}$ which was obtained when sensing of the relative humidity of the relative was performed, the calibrated pressure value $D'_{PRE}$ which was generated in response to the temperature calibration operation, and the calibrated humidity value $D'_{HUMD}$ The gas-concentration calculation circuit 111D performs a calculation to compensate for the baseline resistance value of the gas sensor 10D according to the sensed temperature value $D_{TEMP}$, the calibrated pressure value $D'_{PRE}$, and the calibrated humidity value $D'_{HUMD}$ and then calibrates the gas-concentration value $D_{GAS}$ according to the compensated baseline resistance value to generate a calibrated gas-concentration value $D'_{GAS}$. The calibrated gas-concentration value $D'_{GAS}$ is generated to more accurately reflect the gas concentration in the current environment. The gas-concentration calculation circuit 111D stores the calibrated gas-concentration value $D'_{GAS}$ in the memory 115.

Figure 1D:
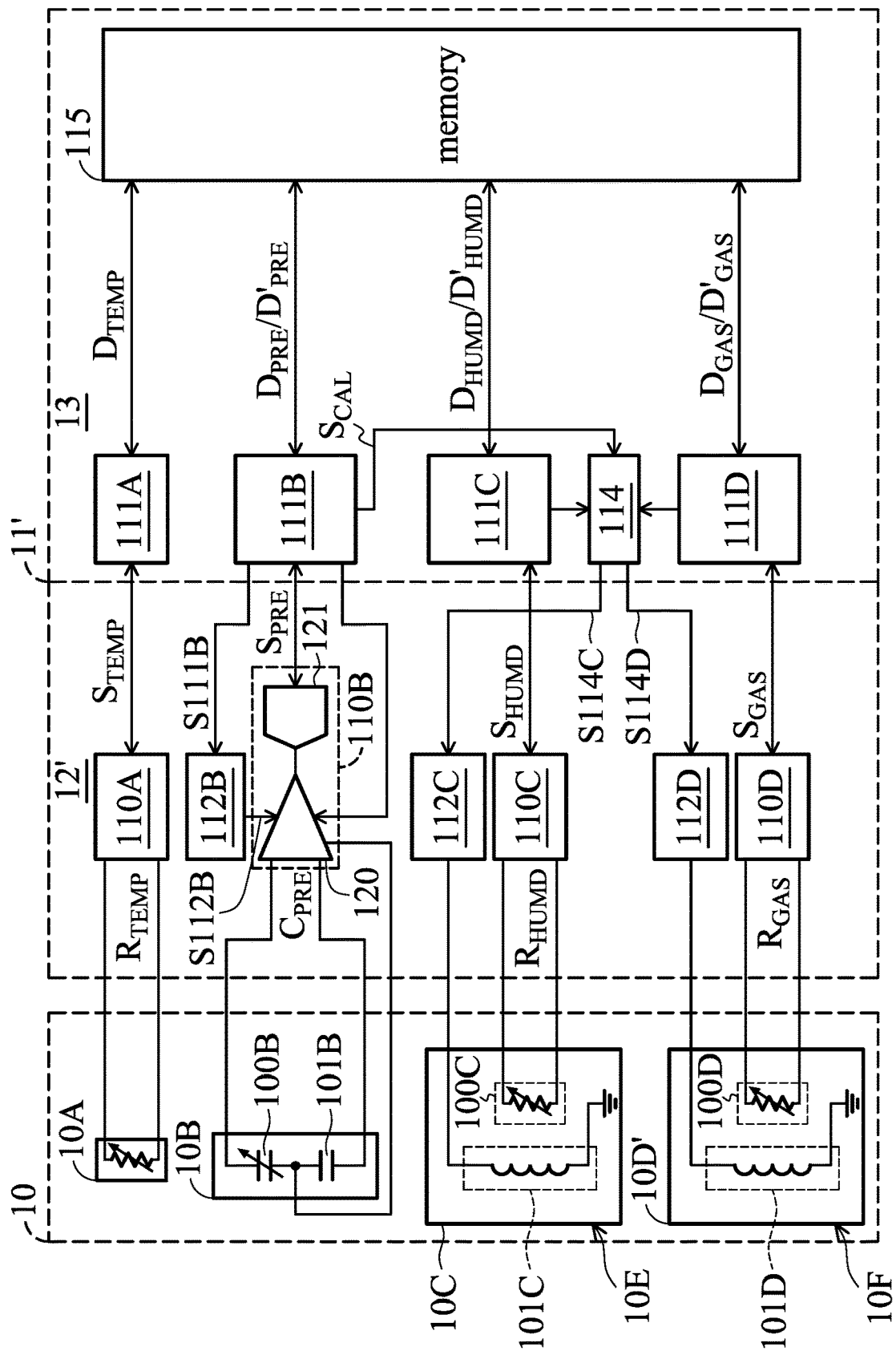
FIG. 1D shows a sensing device according to another embodiment of the present disclosure.

FIG. 1D shows a sensing device according to another embodiment of the present disclosure. The sensing device of the embodiment is similar to the sensing device shown in FIG. 1C and can operate to perform the calibration method shown in FIG. 3A or 3B. The difference between the sensing device of the embodiment shown in FIG. 1D and the sensing device shown in FIG. 1C is explained in the following. Referring to FIGS. 1D and 2, the second environmental sensor 10F of the embodiment is a gas sensor 10D'. The gas sensor 10D' of the embodiment comprises the same second sensing element 100D as the embodiment shown in FIG. 1C and further comprises a second heater 101D. Moreover, in addition to the temperature reading circuit 110A, the pressure reading circuit 110B, the pressure calibration circuit 112B, the humidity reading circuit 110C, the first heating driving circuit 112C, and the gas-concentration reading circuit 110D which are also shown in the embodiment of FIG. 1C, the reading and calibration unit 12' of the processing circuit 11' of the embodiment further comprises a second heating driving circuit 112D. During the process of sensing the gas concentration performed by the gas sensor 10D', the heating control circuit 114 generates a signal S114D to control the second heating driving circuit 112D to output a voltage which is provided to drive the second heater 101D. In response to the voltage, the second heater 101D generates thermal energy to heat the second sensing element 100D and the substrate 20. The gas sensor 10D' of the embodiment performs gas-concentration sensing for obtaining a calibrated gas-concentration value $D'_{GAS}$ in the same manner and process as the previous embodiment. Please refer to the previous embodiment, and the related description will not be repeated.

Figure 4A:
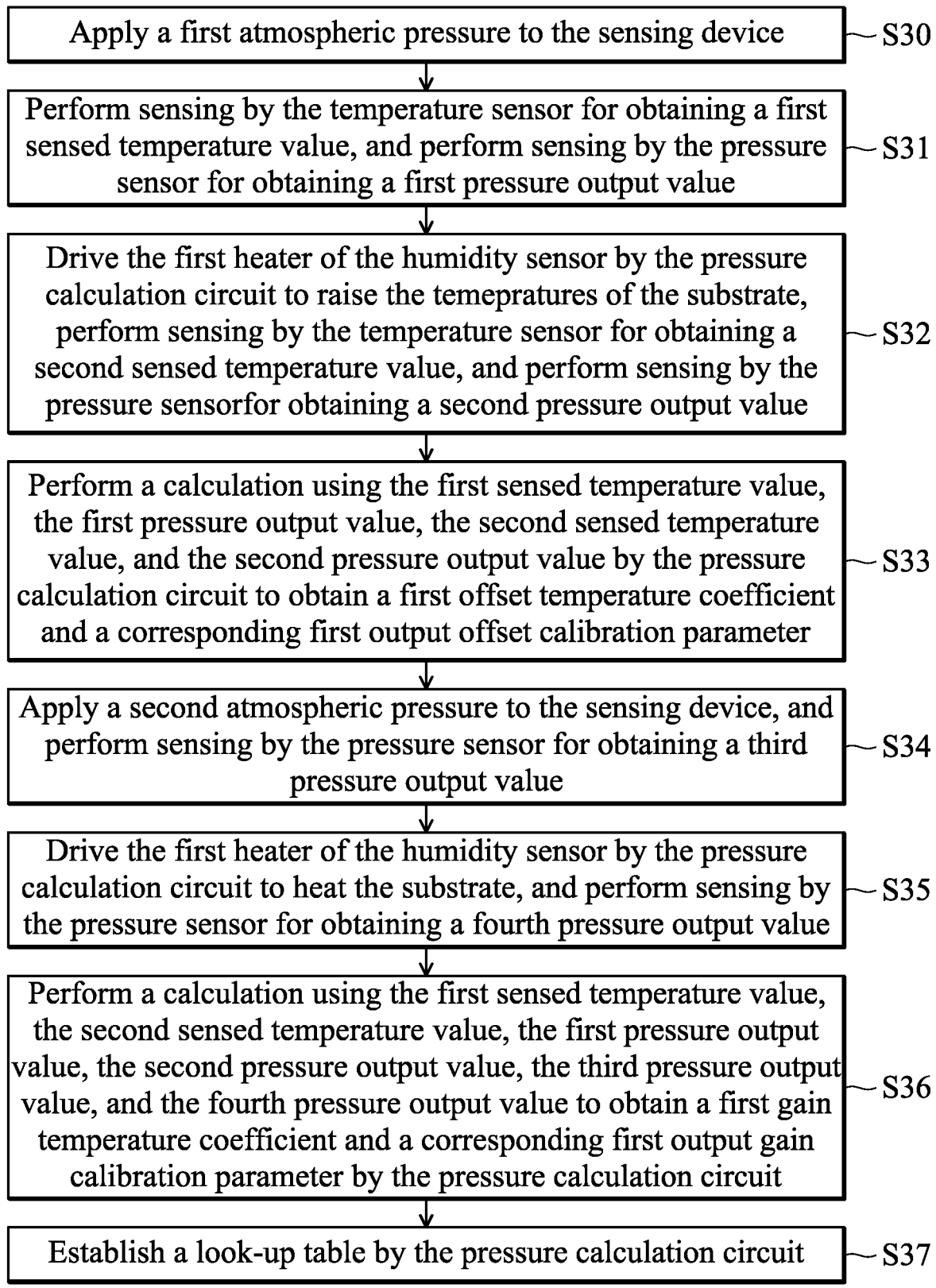
FIG. 4A shows a flowchart of a method for generating temperature calibration parameters according to one embodiment of the present disclosure.

The sensing device of the present disclosure performs a temperature calibration operation according to at least one temperature calibration parameter. FIG. 4A shows a flowchart of a method for generating temperature calibration parameters according to one embodiment of the present disclosure, which may be applicable to the sensing device shown in FIG. 1A, 1B, 1C, or 1D. Referring to FIG. 4A, FIG. 2, and FIG. 1A, 1B, 1C or 1D, when the sensing device 1 creates or updates the temperature calibration parameters, firstly, a first atmospheric pressure P0 is applied to the sensing device 1 (Step S30). That is, the sensing device 1 is disposed in the environment of the first atmospheric pressure P0.

When the sensing device 1 is at the first atmospheric pressure P0, the temperature sensor 10A performs sensing for obtaining a first sensed temperature value $T_{ref}$ and the pressure sensor 10B performs sensing for obtaining a first pressure output value $P_{ref1}$ (Step S31).

Then, the pressure calculation circuit 111B drives the first heater 101C of the humidity sensor 10C through the heating control circuit 114 and the first heating driving circuit 112C, so that the first heater 101C heats the substrate 20. At this time, the temperature sensor 10A performs sensing for obtaining a second sensed temperature value $T_{h1}$, and the pressure sensor 10B performs sensing for obtaining a second pressure output value $P_{h10}$ (Step S32). The pressure calculation circuit 111B performs a calculation using the first sensed temperature value $T_{ref}$ the first pressure output value $P_{ref1}$, the second sensed temperature value $T_{h1}$, and the second pressure output value $P_{h10}$) to obtain a first offset temperature coefficient $TCO_1$ and a first output offset calibration parameter OC1 (Step S33).

Next, in the case where the first heater 101C of the humidity sensor 10C does not operate, a second atmospheric pressure P1 is applied to the sensing device 1, and the pressure sensor 10B performs sensing for obtaining a third pressure output value $P_{ref2}$ (Step S34). At this time, the environmental temperature sensed by the temperature sensor 10A is the first sensed temperature $T_{ref}$ obtained in Step S30. The pressure calculation circuit 111B then drives the first heater 101C of the humidity sensor 10C to heat the substrate 20, and the pressure sensor 10B performs sensing for obtaining a fourth pressure output value $P_{h11}$ (Step S35). Next, the pressure calculation circuit 111B performs a calculation using the first sensed temperature value $T_{ref}$, the second sensed temperature value $T_{h1}$, the first pressure output value $P_{ref1}$ and the second pressure output value $P_{h10}$ corresponding to the first atmospheric pressure P0, and the third pressure output value $P_{ref2}$ and the fourth pressure output value $P_{h11}$ corresponding to the second atmospheric pressure P1 to obtain a first gain temperature coefficient $TCG_1$ and a first output gain calibration parameter GC1 (Step S36).

Figures 5A, 5B, 5C:
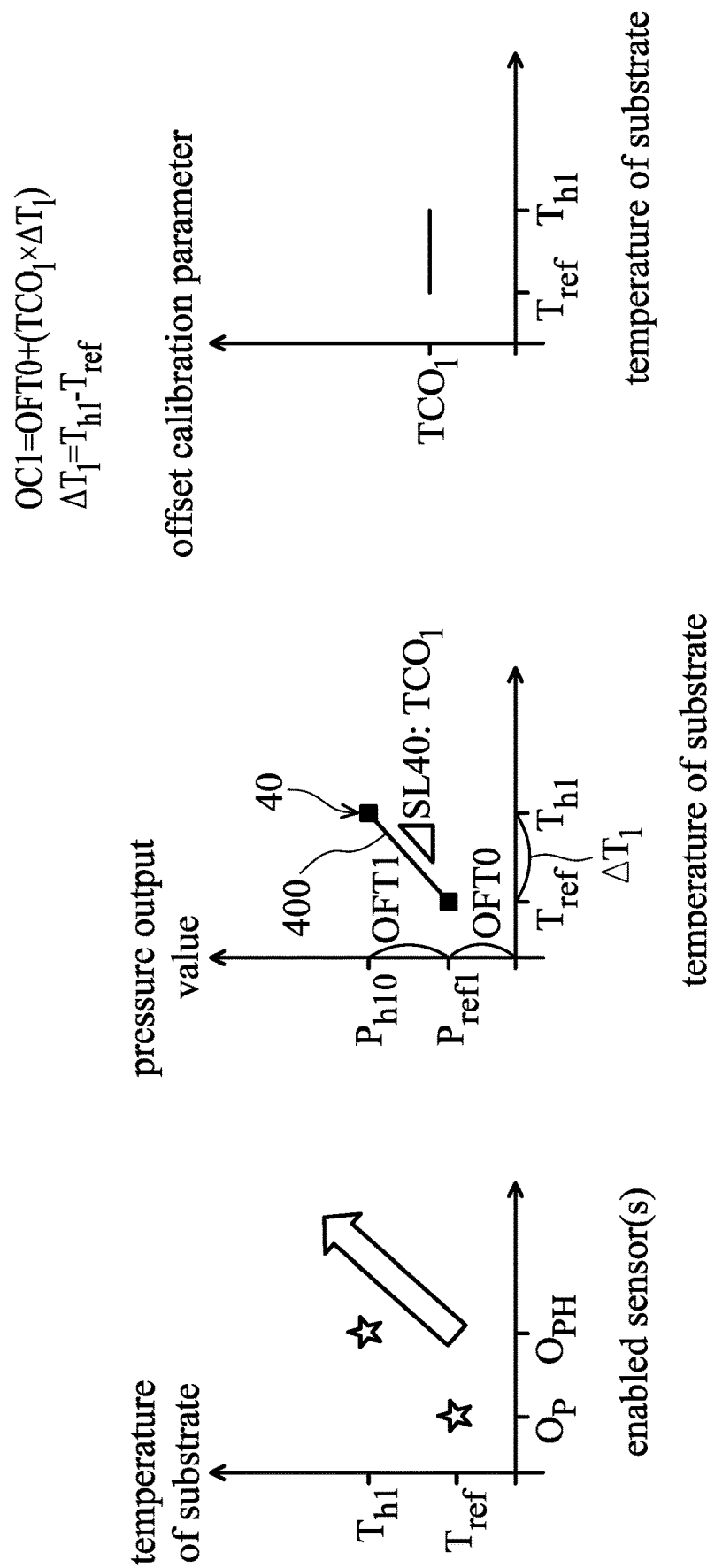
FIG. 5A is a schematic diagram of relationship between operation states of a pressure sensor, a gas sensor, and a humidity sensor and temperature values obtained during operations according to one embodiment of the present disclosure.
FIG. 5B shows a curve depicting the relationship between respective sensed temperature values and corresponding pressure output values according to one embodiment of the present disclosure.
FIG. 5C is a schematic diagram showing relationship between respective sensed temperature values and a offset temperature coefficient according to one embodiment of the present disclosure.

FIG. 5A is a schematic diagram of the relationship between the operating states of the pressure sensor 10B, the gas sensor 10D, and the humidity sensor 10C and the temperature values obtained during the operations. Referring to FIG. 5A, $O_P$ represents the operation state in which only the pressure sensor 10B operates (that is, neither the gas sensor 10D nor the humidity sensor 10C operates or is driven), and $O_{PH}$ represents the operation state in which the pressure sensor 10B and the first heater 101C of the humidity sensor 10C operate.

FIG. 5B shows a curve 40 of the relationship between the sensed temperature values $T_{ref}$ and $T_{h1}$ and the pressure output values $P_{ref1}$ and $P_{h10}$ in the embodiment. The pressure calculation circuit 111B calculates the first pressure difference (that is, the first output offset) OFT1 between the second pressure output value $P_{h10}$ and the first pressure output value $P_{ref1}$ and also calculates the first temperature difference $\Delta T_1$ between the second sensed temperature value $T_{h1}$ and the first sensed temperature value $T_{ref}$. The pressure calculation circuit 111B calculates the ratio of the first pressure difference OFT1 to the first temperature difference $\Delta T_1$ to obtain the slope SL40 of the section 400 of the curve 40. The slope SL40 serves as the first offset temperature coefficient $TCO_1$. FIG. 5C is a schematic diagram showing the relationship between the sensed temperature values $T_{ref}$ and $T_{h1}$ and the first offset temperature coefficient $TCO_1$. Further referring to FIG. 5C, when the temperature of the substrate 20 or the temperature of the environment of the sensing device 1 is a value between the first sensed temperature value $T_{ref}$ and the second sensed temperature value $T_{h1}$, the offset temperature coefficient of the pressure sensor 10B is the first offset temperature coefficient $TCO_1$.

FIG. 6A shows the pressure output values and their changes obtained under different temperatures of the environments or substrate 20 when a first atmospheric pressure P0 or a second atmospheric pressure P1 is applied to the sensing device 1. In FIG. 6A, the curve C1 represents the change in the pressure output value which is obtained when a pressure that is between the first atmospheric pressure P0 and the second atmospheric pressure P1 is applied to the sensing device 1 while the environmental temperature or the temperature of the substrate 20 is the first sensed temperature value $T_{ref}$. That is, the curve C1 represents the change between the first pressure output value $P_{ref1}$ and the third pressure output value $P_{ref2}$. The curve C2 represents the change in the pressure output value which is obtained when a pressure that is between the first atmospheric pressure P0 and the second atmospheric pressure P1 is applied to the sensing device 1 while the environmental temperature or the temperature of the substrate 20 is the second sensed temperature value $T_{h1}$. That is, the curve C2 represents the change between the second pressure output value $P_{h10}$ and the fourth pressure output value $P_{h1}$. The pressure calculation circuit 111B performs a calculation to obtain the slope SL50 of the curve C1 and the slope SL51 of the curve C2. The pressure calculation circuit 111B uses the slope SL50 as a reference output gain $G_0$ of the pressure sensor 10B and further uses the slope SL51 as the first output gain $G_1$ of the pressure sensor 10B.

FIG. 6B shows the curve 50 of the output gains $G_0$ and $G_1$ corresponding to the situation where the environmental temperature or the temperature of the substrate 20 is the sensed temperature values $T_{ref}$ and $T_{h1}$. The pressure calculation circuit 111B performs a calculation to obtain the first gain difference $\Delta G1$ between the first output gain $G_1$ and the reference output gain $G_0$ and the first temperature difference $\Delta T_1$ between the second sensed temperature value $T_{h1}$ and the first sensed temperature value $T_{ref}$. The pressure calculation circuit 111B further performs a calculation to obtain the ratio of the first gain difference $\Delta G1$ to the first temperature difference $\Delta T_1$, that is, to obtain the slope SL53 of the section 500 of the curve 50. The slope SL53 serves as the first gain temperature coefficient $TCG_1$. FIG. 6C is a schematic diagram showing the relationship between the sensed temperature values $T_{ref}$ and $T_{h1}$ and the first gain temperature coefficient $TCG_1$. As shown in FIG. 6C, when the environmental temperature of the sensing device 1 or the temperature of the substrate 20 is a value between the first sensed temperature value $T_{ref}$ and the second sensed temperature value $T_{h1}$, the gain temperature coefficient of the pressure sensor 10B is the first gain temperature coefficient TCG1.

When the temperature calibration operation of the pressure sensor 10B is performed, the offset temperature coefficient and the gain temperature coefficient of the pressure sensor 10B need to be considered. The output voltage of the pressure reading circuit 110B at this time is represented by VO, which is expressed as:

$$VO = [V_{SENS} + OFT + (TCO \times \Delta T) - (OC)] \times [GAIN + (TCG \times \Delta T)] \quad \text{(Equation 1)}$$

Wherein, $V_{SENS}$ represents the output voltage of the pressure sensor 10B, OFT represents the output offset voltage of the pressure reading circuit 110B, and GAIN represents the output gain of the pressure sensor 10B.

In the embodiment of the present disclosure, in order to eliminate the influence of the temperature on the pressure sensor 10B, the temperature calibration operation of the sensing device 1 is performed based on the first sensed temperature value $T_{ref}$. When the environmental temperature of the sensing device 1 or the temperature of the substrate 20 is the first sensed temperature value $T_{ref}$, the output voltage of the pressure reading circuit 110B is represented by $VO_{ref}$, which is expressed as:

$$VO_{ref} = [V_{SENS} + OFT0 - (OC0)] \times [G_0] \quad \text{(Equation 2)}$$

Wherein, OFT0 represents the voltage output reference offset of the pressure reading circuit 110B at the first sensed temperature value $T_{ref}$. OC0 represents the output offset calibration parameter of the pressure sensor 10B at the first sensed temperature value $T_{ref}$. At this time, when OC0 which is equal to OFT0 (OC0=OFT0) is applied into Equation 2, the output offset voltage is calibrated.

When the environmental temperature of the sensing device 1 or the temperature of the substrate 20 is the second sensed temperature value $T_{h1}$, according to Equation 2 and by using the voltage output reference offset OFT0, the output voltage of the pressure reading circuit 110B is represented by VO1, which is expressed as:

$$VO1=[V_{SENS}+OFT0+(TCO_1 \times \Delta T_1)-(OC1)] \times [GC1+(TCG_1 \times \Delta T_1)]$$ (Equation 3)

Wherein, $\Delta T_1 = T_{h1} - T_{ref}$.

At this time, comparing Equation 1 and Equation 3, if OC1 which is equal to OFT0+($TCO_1 \times \Delta T_1$) (i.e., OC1=OFT0+($TCO_1 \times \Delta T_1$)) is applied, the influence of the offset temperature coefficient $TCO_1$ can be eliminated, and the output offset voltage can be calibrated. Moreover, if GC1 which is equal to $G_0$-($TCG_1 \times \Delta T_1$) (i.e., GC1=$G_0$-($TCG_1 \times \Delta T_1$)) is applied, the influence of the gain temperature coefficient $TCG_1$ can be eliminated, such that the pressure sensing gain can be maintained at the reference output gain $G_0$, and the temperature drifting occurred in the output gain can be calibrated. According to the above embodiment, the difference between the output offset calibration parameters OC0 and OC1 is ($TCO_1 \times \Delta T_1$), and the difference between the reference output gain $G_0$ and the first output gain calibration parameter GC1 is ($TCG_1 \times \Delta T_1$).

After obtaining the first output offset calibration parameter OC1 and the first output gain calibration parameter GC1, the pressure calculation circuit 111B establishes a look-up table (Step S37), which comprises the relationship between the second sensed temperature value $T_{h1}$ relative to the first output offset calibration parameter OC1 and the first output gain calibration parameter GC1. The pressure calculation circuit 111B stores the look-up table in the memory 115.

Figures 1, 4B:
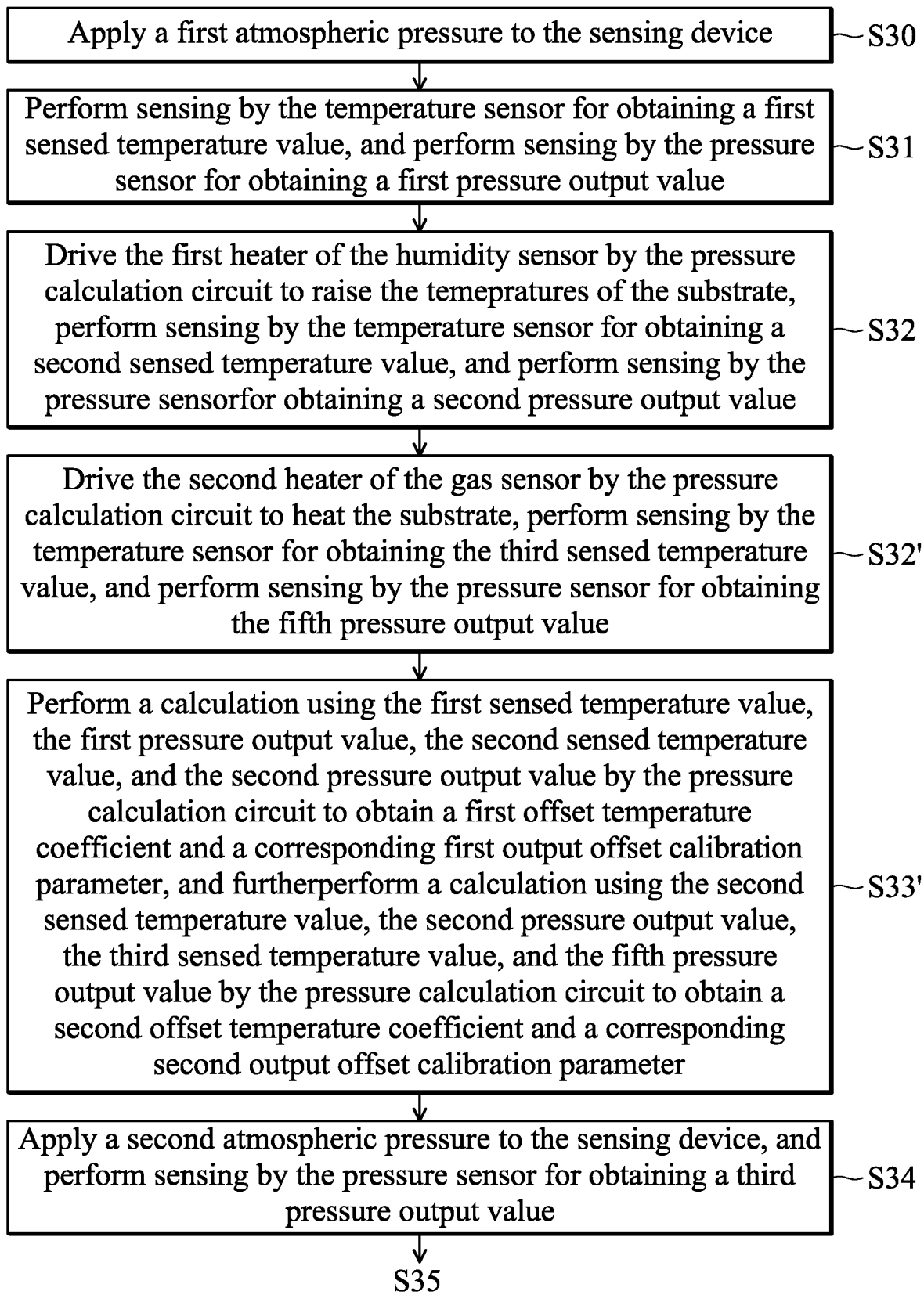
Figures 2, 4B:
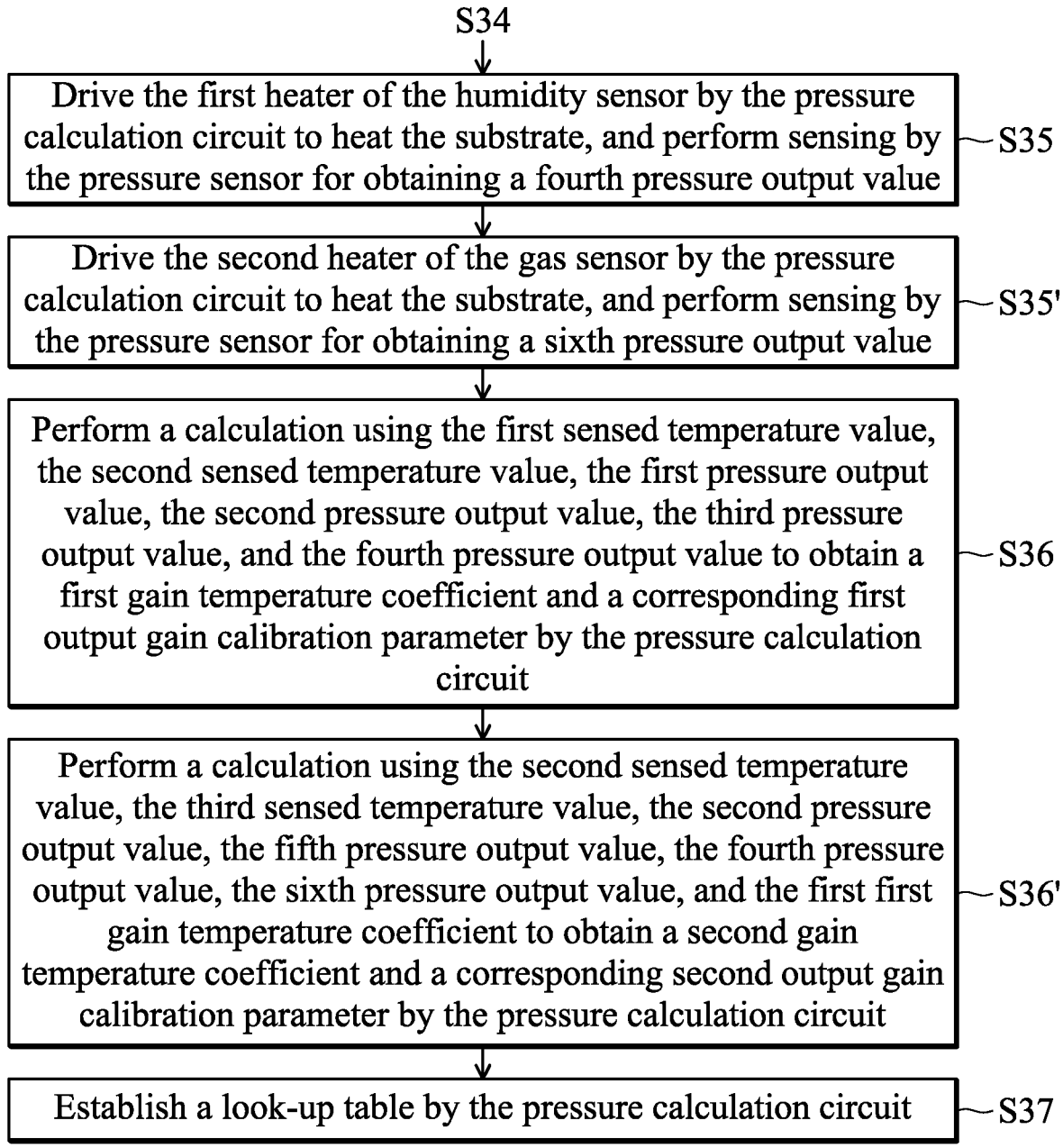

The sensing device of the present disclosure performs the temperature calibration operation based on at least one temperature calibration parameter. FIGS. 4B-1 and 4B-2 show a method for generating temperature calibration parameters according to another embodiment of the present disclosure. The method may be applied to the sensing device shown in FIG. 1A, 1B, 1C or 1D. Referring to FIGS. 4B-1 and 4B-2, FIG. 2, and FIG. 1A, 1B, 1C, or 1D, the method of generating temperature calibration parameters in the embodiment is similar to that shown in FIG. 4A. In addition to the first output offset calibration parameter and the first output gain calibration parameter, the temperature calibration parameters further comprise a second output offset calibration parameter and a second output gain calibration parameter. The difference between the method of the embodiment and the methods shown in FIG. 4A is explained in the following paragraphs.

After performing Step S32 as shown in FIG. 4A, Step S32' is further performed in the method of the embodiment. In Step S32' where the first atmospheric pressure P0 is applied to the sensing device 1, the pressure calculation circuit 111B drives the second heater 101D of the gas sensor 10D through the heating control circuit 114 and the second heating driving circuit 112D, so that the second heater 101D heats the substrate 20. At this time, the temperature sensor 10A performs sensing for obtaining the third sensed temperature value $T_{h2}$, and the pressure sensor 10B performs sensing for obtaining the fifth pressure output value $P_{h20}$. Step S33' of the embodiment is similar to Step S33 shown in FIG. 4A. However, in Step S33' of the embodiment, the pressure calculation circuit 111B performs a calculation further using the second sensed temperature value $T_{h1}$, the second pressure output value $P_{h10}$, the third sensed temperature value $T_{h2}$, and the fifth pressure output value $P_{h20}$ to obtain a second offset temperature coefficient $TCO_2$ and a second output offset calibration parameter OC2.

On the other hand, after the Steps S34 and Step S35 as the steps shown in FIG. 4A are performed, Step S35' is further performed in the embodiment. In the condition where the second atmospheric pressure P1 is applied to the sensing device 1, the pressure calculation circuit 111B drives the second heater 101D of the gas sensor 10D to heat the substrate 20, and the pressure sensor 10B performs sensing for obtaining a sixth pressure output value $P_{h21}$. At this time, the environmental temperature sensed by the temperature sensor 10A is the third sensed temperature value $T_{h2}$ in Step S32'. In the embodiment, after Step S36 that is the same as the step shown in FIG. 4A is performed, Step S36' is further performed. In Step S36', the pressure calculation circuit 111B performs a calculation using the second sensed temperature value $T_{h1}$, the third sensed temperature value $T_{h2}$, the second pressure output value $P_{h10}$ and the fifth pressure output value $P_{h20}$ corresponding to the first atmospheric pressure P0, the fourth pressure output value $P_{h11}$ and the sixth pressure output value $P_{h21}$ corresponding to the second atmospheric pressure P1, and the first gain temperature coefficient $TCG_1$ to obtain a second gain temperature coefficient TCG2 and a second output gain calibration parameter GC2.

Figures 7A, 7B, 7C:
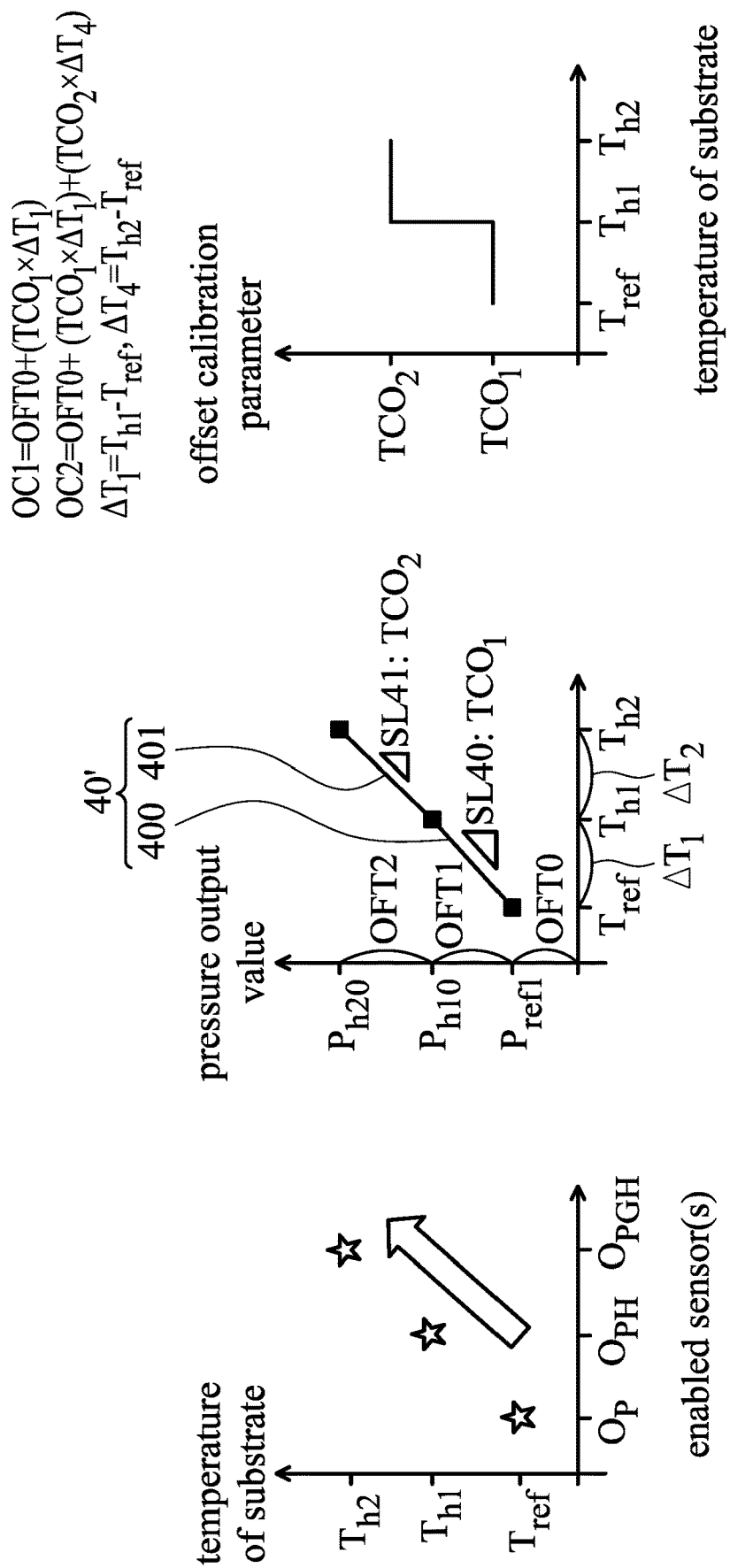
FIG. 7A is a schematic diagram of relationship between operation states of a pressure sensor, a gas sensor, and a humidity sensor and temperature values obtained during the operation according to another embodiment of the present disclosure.
FIG. 7B shows a curve depicting the relationship between respective sensed temperature values and corresponding pressure output values according to another embodiment of the present disclosure.
FIG. 7C is a schematic diagram showing relationship between respective sensed temperature values and corresponding offset temperature coefficients according to another embodiment of the present disclosure.

FIG. 7A is a schematic diagram of the relationship between the operating states of the pressure sensor 10B, the second heater 101D of the gas sensor 10D, and the first heater 101C of the humidity sensor 10C and the temperature values obtained during the operations. Referring to FIG. 7A, $O_P$ represents the operation state in which only the pressure sensor 10B operates (that is, neither the gas sensor 10D nor the humidity sensor 10C operates or is driven), $O_{PH}$ represents the operation state in which the pressure sensor 10B and the first heater 101C of the humidity sensor 10C operate, and $O_{PGH}$ represents the operation state in which that all the pressure sensor 10B, the second heater 101D of the gas sensor 10D, and the first heater 101C of the humidity sensor 10C operate.

FIG. 7B shows a curve 40' of the relationship between the sensed temperature values $T_{ref}$, $T_{h1}$, and $T_{h2}$ and the pressure output values $P_{ref1}$, $P_{h10}$, and $P_{h20}$ in the embodiment. The pressure calculation circuit 111B calculates the first pressure difference (that is, the first output offset) OFT1 between the second pressure output value $P_{h10}$ and the first pressure output value $P_{ref1}$ and also calculates the first temperature difference $\Delta T_1$ between the second sensed temperature value $T_{h1}$ and the first sensed temperature value $T_{ref}$. The pressure calculation circuit 111B calculates the ratio of the first pressure difference OFT1 to the first temperature difference $\Delta T1$ to obtain the slope SL40 of the section 400 of the curve 40'. The slope SL40 serves as the first offset temperature coefficient $TCO_1$. The pressure calculation circuit 111B calculates the second pressure difference (that is, the second output offset) OFT2 between the fifth pressure output value $P_{h20}$ and the second pressure output value $P_{h10}$ and also calculates the second temperature difference $\Delta T_2$ between the third sensed temperature value $T_{h2}$ and the second sensed temperature value $T_{h1}$. The pressure calculation circuit 111B calculates the ratio of the second pressure difference OFT2 to the second temperature difference $\Delta T2$ to obtain the slope SL41 of the section 401 of the curve 40'. The slope SL41 serves as the second offset temperature coefficient $TCO_2$.

FIG. 7C is a schematic diagram showing the relationship between the sensed temperature values $T_{ref}$, $T_{h1}$, and $T_{h2}$ and the first and second offset temperature coefficients $TCO_1$ and $TCO_2$. Further referring to FIG. 7C, when the temperature of the substrate 20 or the environmental temperature of the sensing device 1 is a value between the first sensed temperature value $T_{ref}$ and the second sensed temperature value $T_{h1}$, the offset temperature coefficient of the pressure sensor 10B is the first offset temperature coefficient $TCO_1$. When the temperature of the substrate 20 or the environmental temperature of the sensing device 1 is a value between the second sensed temperature value $T_{h1}$ and the third sensed temperature value $T_{h2}$, the offset temperature coefficient of the pressure sensor 10B is the second offset temperature coefficient $TCO_2$.

FIG. 8A shows the pressure output values and their changes obtained under different temperatures of the environments or substrate 20 when a first atmospheric pressure P0 or a second atmospheric pressure P1 is applied to the sensing device 1. In FIG. 8A, the curve C1 represents the change in the pressure output value which is obtained when a pressure that is between the first atmospheric pressure P0 and the second atmospheric pressure P1 is applied to the sensing device 1 while the environmental temperature or the temperature of the substrate 20 is the first sensed temperature value $T_{ref}$. That is, the curve C1 represents the changes between the first pressure output value $P_{ref1}$ and the third pressure output value $P_{ref2}$. The curve C2 represents the change in the pressure output value which is obtained when a pressure that is between the first atmospheric pressure P0 and the second atmospheric pressure P1 is applied to the sensing device 1 while the environmental temperature or the temperature of the substrate 20 is the second sensed temperature value $T_{h1}$. That is, the curve C2 represents the change between the second pressure output value $P_{h10}$ and the fourth pressure output value $P_{h11}$. The curve C3 represents the change in the pressure output value which is obtained when a pressure that is between the first atmospheric pressure P0 and the second atmospheric pressure P1 is applied to the sensing device 1 while the environmental temperature or the temperature of the substrate 20 is the third sensed temperature value $T_{h2}$. That is, the curve C3 represents the change between the fifth pressure output value $P_{h20}$ and the sixth pressure output value $P_{h21}$. The pressure calculation circuit 111B performs a calculation to obtain the slope SL50 of the curve C1, the slope SL51 of the curve C2, and the slope SL52 of the curve C2. The pressure calculation circuit 111B uses the slope SL50 as the reference output gain $G_0$ of the pressure sensor 10B, uses the slope SL51 as the first output gain $G_1$ of the pressure sensor 10B, and further uses the slope SL52 as the second output gain $G_2$ of the pressure sensor 10B.

FIG. 8B shows the curve 50' of the output gains $G_0$, $G_1$, and $G_2$ corresponding to the situation where the environmental temperature of the substrate 20 is the sensed temperature values $T_{ref}$, $T_{h1}$, and $T_{h2}$. The pressure calculation circuit 111B performs a calculation to obtain the first gain difference $\Delta G1$ between the first output gain $G_1$ and the reference output gain $G_0$ and the first temperature difference $\Delta T_1$ between the second sensed temperature value $T_{h1}$ and the first sensed temperature value $T_{ref}$. The pressure calculation circuit 111B further performs a calculation to obtain the ratio of the first gain difference $\Delta G1$ to the first temperature difference $\Delta T_1$, that is, to obtain the slope SL53 of the section 500 of the curve 50'. The slope SL53 serves as the first gain temperature coefficient $TCG_1$. The pressure calculation circuit 111B performs a calculation to obtain the second gain difference $\Delta G2$ between the second output gain $G_2$ and the first output gain $G_1$ and the second temperature difference $\Delta T_2$ between the third sensed temperature $T_{h2}$ and the second sensed temperature value $T_{h1}$. The pressure calculation circuit 111B performs a calculation to obtain the ratio of the second gain difference $\Delta G2$ to the second temperature difference $\Delta T_2$, that is, to obtain the slope SL54 of the section 501 of the curve 50'. The slope SL54 serves as the second gain temperature coefficient $TCG_2$.

FIG. 8C is a schematic diagram showing the relationship between the sensed temperature values $T_{ref}$, $T_{h1}$, and $T_{h2}$ and the gain temperature coefficients $TCG_1$ and $TCG_2$. As shown in FIG. 8C, when the environmental temperature of the sensing device 1 or the temperature of the substrate 20 is a value between the first sensed temperature value $T_{ref}$ and the second sensed temperature value $T_{h1}$, the gain calibration parameter of the pressure sensor 10B is the first gain temperature coefficient $TCG_1$. When the environmental temperature of the sensing device 1 or the temperature of the substrate 20 is a value between the second sensed temperature value $T_{h1}$ and the third sensed temperature value $T_{h2}$, the gain temperature coefficient of the pressure sensor 10B is the second gain temperature coefficient $TCG_2$.

When the temperature calibration operations of the pressure sensor 10B is performed, the offset temperature coefficients and the gain temperature coefficients of the pressure sensor 10B need to be considered. The output voltage of the pressure reading circuit 110B at this time is VO, which is expressed as:

$$VO=[V_{SENS}+OFT+(TCO \times \Delta T)-(OC)] \times [GAIN+(TCG \times \Delta T)] \quad \text{(Equation 1)}$$

Wherein, $V_{SENS}$ represents the output voltage of the pressure sensor 10B, OFT represents the output offset voltage of the pressure reading circuit 110B, and GAIN represents the output gain of the pressure sensor 10B.

In the embodiment of the present disclosure, in order to eliminate the influence of the temperature on the pressure sensor 10B, the temperature calibration operation of the sensing device 1 is performed based on the current first sensed temperature value $T_{ref}$. When the environmental temperature or the temperature of the substrate 20 is the first sensed temperature value $T_{ref}$, the output voltage of the pressure reading circuit 110B is VOref, which is expressed as:

$$VO_{ref}=[V_{SENS}+OFT0-(OC0)] \times [G_0] \quad \text{(Equation 2)}$$

Wherein, OFT0 represents the voltage output reference offset of the pressure reading circuit 110B at the first sensed temperature value $T_{ref}$. OC0 represents the output offset calibration parameter of the pressure sensor 10B at the first sensed temperature value $T_{ref}$. At this time, when OC0 is equal to OFT0 (OC0=OFT0), the output offset voltage is calibrated.

When the temperature of the environment of the sensing device 1 or the temperature of the substrate 20 is the second sensed temperature value $T_{h1}$, according to Equation 2 and by using the voltage output reference offset OFT0, the output voltage of the pressure reading circuit 110B is VO1, which is expressed as:

$$VO1=[V_{SENS}+OFT0+(TCO_1 \times \Delta T_1)-(OC1)] \times [GC1+(TCG_1 \times \Delta T_1)] \quad \text{(Equation 3)}$$

Wherein, $\Delta T_1 = T_{h1} - T_{ref}$.

At this time, comparing Equation 1 and Equation 3, if $OC1 = OFT0 + (TCO_1 \times \Delta T_1)$, the influence of the offset temperature coefficient $TCO_1$ can be eliminated, and the output offset voltage can be calibrated. Moreover, if $GC1 = G_0 -$ (TCG$_1$×ΔT$_1$), the influence of the gain temperature coefficient TCG$_1$ can be eliminated, such that the pressure sensing gain can be maintained at the reference output gain G$_0$, and the temperature drifting occurred in the output gain can be calibrated. According to the above description, the difference between the output offset calibration parameters OC0 and OC1 is (TCO$_1$×ΔT$_1$), and the difference between the reference output gain G$_0$ and the first output gain calibration parameter GC1 is (TCG$_1$×ΔT$_1$).

When the temperature of the environment of the sensing device 1 or the temperature of the substrate 20 is at the third temperature value T$_{h2}$, according to Equation 1 and by using the voltage output reference offset OFTO, the output voltage of the pressure reading circuit 110B is VO2, which is expressed as:

$$VO2=[V_{SENS}+OFT0+(TCO_1×ΔT_1)+(TCO_2×ΔT_4)-(OC2)]×[GC2+(TCG_1×ΔT_1)+(TCG_2×ΔT_4)] \quad \text{(Equation 4)}$$

Wherein, ΔT$_4$=T$_{h2}$−T$_{ref}$.

At this time, comparing Equation 1 and Equation 4, if OC2 which is equal to OFT0+(TCO$_1$×ΔT$_1$)+(TCO$_2$×ΔT$_4$) (i.e., OC2=OFT0+(TCO$_1$×ΔT$_1$)+(TCO$_1$×ΔT$_4$)) is applied, the influence of the offset temperature coefficient TCO$_2$ can be eliminated, and the output offset voltage can be calibrated. Moreover, if GC2 which equal to G$_0$−(TCG$_1$×ΔT$_1$)−(TCG$_2$×ΔT$_4$) (i.e., GC2=G$_0$−(TCG$_1$×ΔT$_1$)−(TCG$_2$×ΔT$_4$)) is applied, the influence of the gain temperature coefficient TCG$_2$ can be eliminated, such that the pressure sensing gain can be maintained at the reference output gain G$_0$, and the temperature drifting occurred in the output gain can be calibrated. According to the above description, the difference between the output offset correction parameters OC0 and OC2 is (TCO$_1$×ΔT$_1$)+(TCO$_2$×ΔT$_4$), and the difference between the reference output gain G$_0$ and the second output gain calibration parameter GC2 is (TCG$_1$×ΔT$_1$)+(TCG$_2$×ΔT$_4$).

According to the above description, the pressure calculation circuit 111B obtains the first offset temperature coefficient TCO$_1$ and the second offset temperature coefficient TCO$_2$. The pressure calculation circuit 111B performs a calculation using the first offset temperature coefficient TCO$_1$ to obtain the first output offset calibration parameter OC1; that is, the pressure calculation circuit 111B obtains the first output offset calibration parameter OC1 from the voltage output reference output offset OFT0 plus the difference (TCO$_1$×ΔT$_1$) between the output offset calibration parameters OC0 and OC1. The pressure calculation circuit 111B also performs a calculation using the second offset temperature coefficient TCO$_2$ to obtain the second output offset calibration parameter OC2; that is, the pressure calculation circuit 111B obtains the second output offset calibration parameter OC2 from the reference output offset voltage OFT0 plus the difference (TCO$_1$×ΔT$_1$)+(TCO$_2$×ΔT$_4$) between the output offset calibration parameters OC0 and OC2. Moreover, the pressure calculation circuit 111B performs a calculation to obtain the first gain temperature coefficient TCG$_1$ and the second gain temperature coefficient TCG$_2$ and further calculates the first output gain calibration parameter GC1 and the second output gain calibration parameter GC2. In detail, the pressure calculation circuit 111B obtains the first output gain calibration parameter GC1 from the reference output gain G$_0$ minus the difference (TCG$_1$×ΔT$_1$) between the reference output gain G$_0$ and the first output gain calibration parameter GC1. The pressure calculation circuit 111B obtains the second output gain calibration parameter GC2 from the reference gain G$_0$ minus the difference (TCG$_1$×ΔT$_1$)+(TCG$_2$×ΔT$_4$) between the reference output gain G$_0$ and the second output gain calibration parameter GC2.

After obtaining the first and second output offset calibration parameters OC1 and OC2 and the first and second output gain calibration parameters GC1 and GC2, the pressure calculation circuit 111B establishes a look-up table (step S37). The established look-up table comprises the relationship between the second sensed temperature value T$_{h1}$ relative to the first output offset calibration parameter OC1 and the first output gain calibration parameter GC1 and further comprises the relation between the third sensed temperature value T$_{h2}$ relative to the second output offset calibration parameter OC2 and the second output gain calibration parameter GC2. The pressure calculation circuit 111B stores the look-up table in the memory 115.

Figure 9:
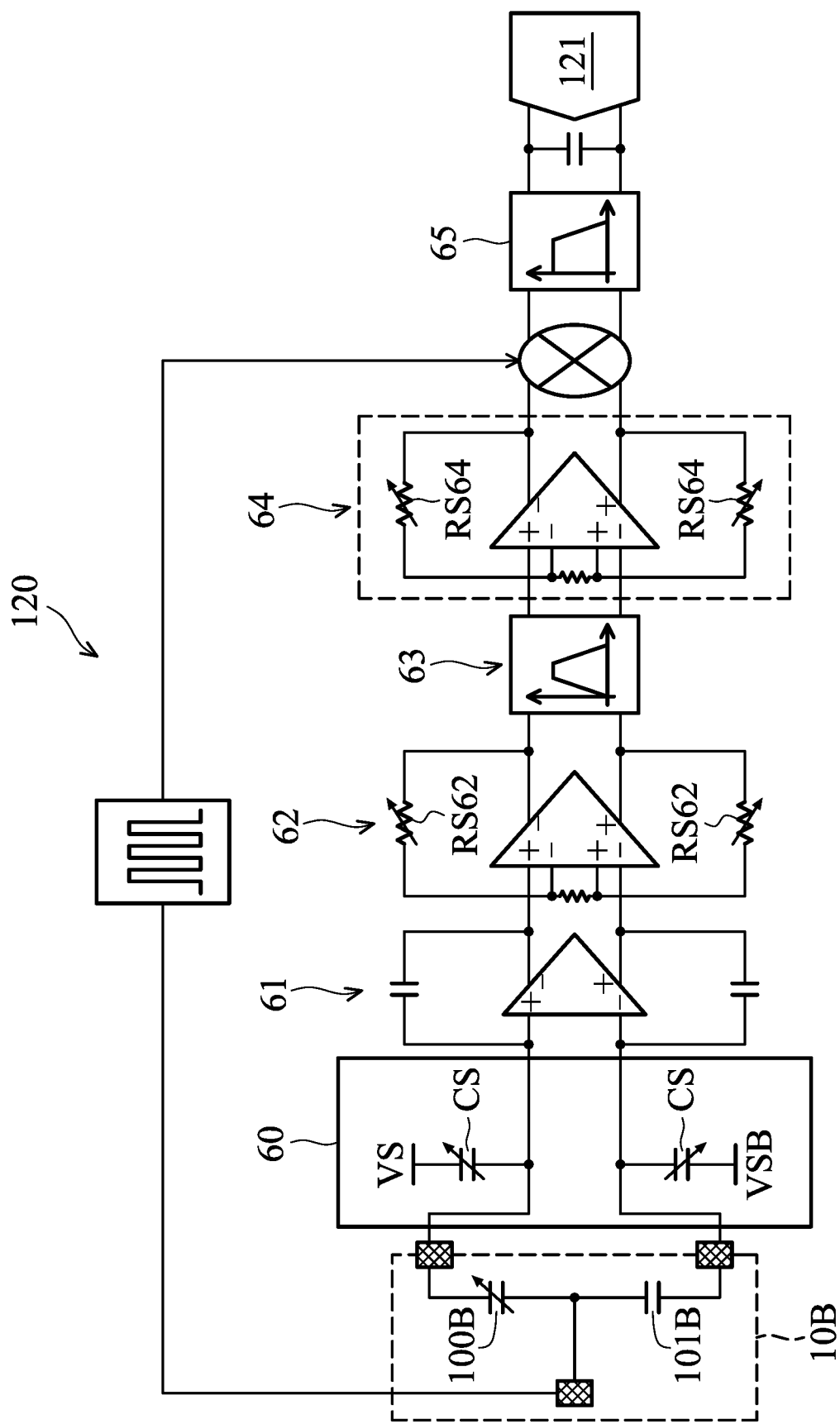
FIG. 9 shows a circuit architecture of an analog front-end circuit shown in FIGS. 1A~1D according to an embodiment of the present disclosure.

The following will describe how the first and second output offset calibration parameters OC1 and OC2 and the first and second output gain calibration parameters GC1 and GC2 are obtained from the pressure calibration circuit 112B and the analog front-end circuit 120. Referring to FIG. 9, the analog front-end circuit 120 comprises a plurality of circuit stages. The analog front-end circuit 120 receives the pressure sensing voltage V$_{PRE}$ and generates an output voltage VO to the delta-sigma modulated analog-to-digital converter 121. These circuit stages comprise an output offset calibration circuit 60, two amplifying circuits 61 and 62, filters 63 and 65, and an output gain calibration circuit 64. When the temperature calibration operation is performed, the pressure calculation circuit 111B accesses the memory 115 and uses the look-up table to obtain the output offset calibration parameters and the output gain calibration parameters corresponding to the current sensed temperature value, for example, the first output offset calibration parameter OC1 and the first output gain calibration parameter GC1 corresponding to the second sensed temperature value T$_{h1}$. The pressure calculation circuit 111B generates the control signal S111B according to the first output offset calibration parameter OC1 and the first output gain calibration parameter GC1 and provides the control signal S111B to the pressure calibration circuit 112B. The pressure calibration circuit 112B generates the calibration signal S112B according to the control signal S111B. The analog front-end circuit 120 changes the operation voltage V$_S$ and V$_{SB}$ or the capacitance values of the capacitors C$_S$ of the output offset calibration circuit 60 according to the calibration signal S112B to calibrate the output offset voltage. Moreover, the analog front-end circuit 120 changes the resistance values of the resistors RS64 of the output gain calibration circuit 64 according to the calibration signal S112B to adjust the output gain, thereby eliminating the temperature drifting of the gain. In other embodiments, the amplifying circuit 62 and the output gain calibration circuit 64 operate for the gain calibration. For example, the amplifying circuit 62 performs a coarse gain calibration by changing the resistance values of the resistors RS62, and the output gain calibration circuit 64 performs a fine gain calibration by changing the resistance values of the resistors RS64.

Figure 10:
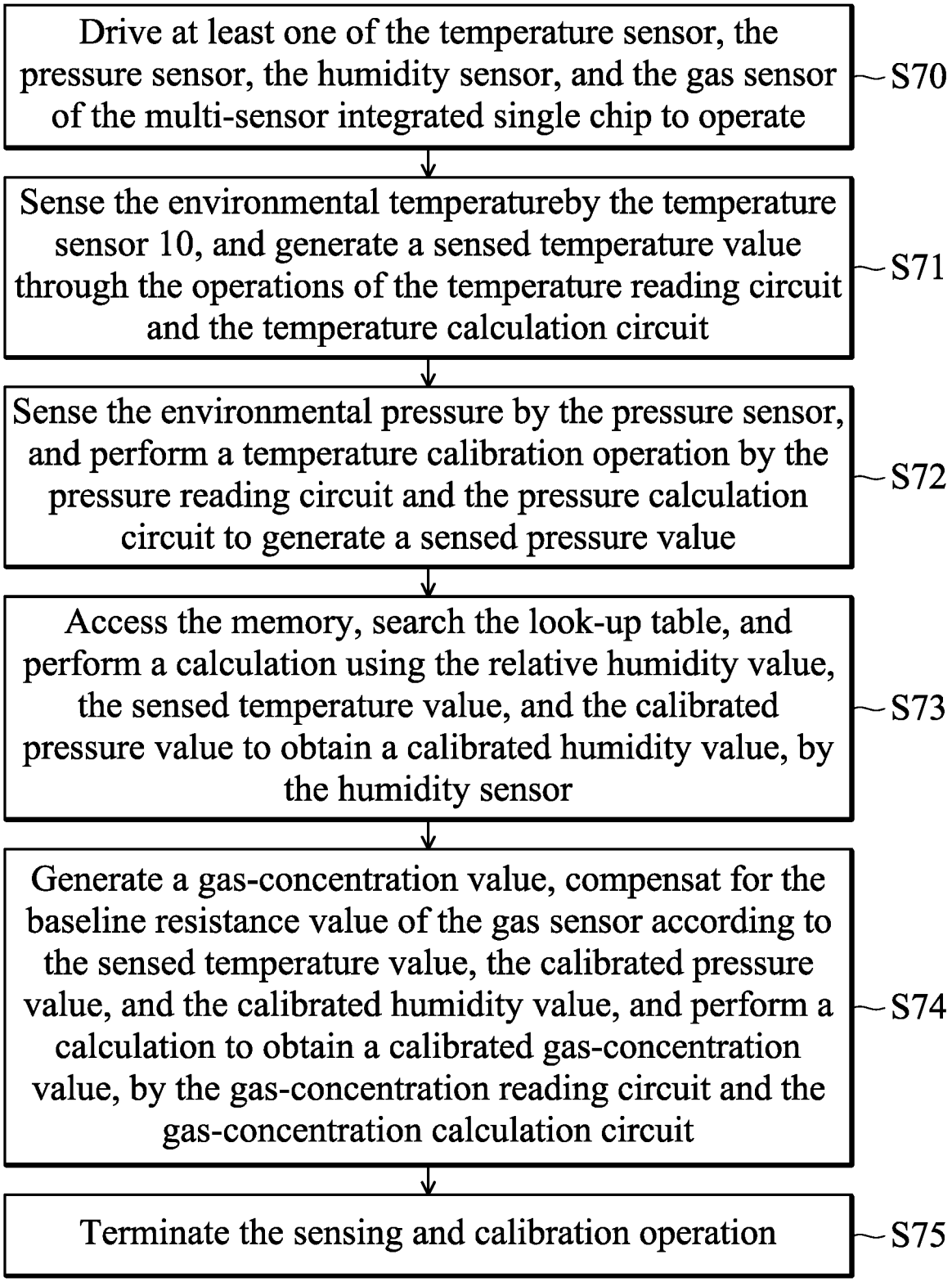
FIG. 10 shows a calibration method according to an embodiment of the present disclosure.

FIG. 10 shows a calibration method according to an embodiment of the present disclosure. The calibration method in FIG. 10 can be applied to the sensing device of the embodiment shown in any one of FIGS. 1A~1D. Referring to FIG. 10, the multi-sensor integrated single chip 10 comprises a temperature sensor 10A, a pressure sensor 10B, a humidity sensor 10C and a gas sensor 10D, and at least one of them is driven to operate (Step S70). When the multi-sensor integrated single chip 10 performs the sensing of the humidity of the environmental, the humidity sensor 10C may operate alone, that is, only the humidity sensor 10C may be driven. When the multi-sensor integrated single chip 10 performs the sensing of the gas concentration of the environmental, since the sensing of the gas concentration is affected by the humidity of the environmental, the humidity sensor 10C and the gas sensor 10D need to work together, that is, both the humidity sensor 10C and the gas sensor 10D are driven at the same time. When at least one of the humidity sensor 10C and the gas sensor 10D operates, at least one of the first and second heaters 101C and 101D is also driven at the same time, so that the environmental temperature of the multi-sensor integrated single chip 10 rises. The temperature sensor 10A senses the environmental temperature, a sensed temperature value $D_{TEMP}$ is generated through the operations of the temperature reading circuit 110A and the temperature calculation circuit 111A (Step S71). The pressure sensor 10B senses the environmental pressure, and a temperature calibration operation is performed by the pressure reading circuit 110B and the pressure calculation circuit 111B to generate a sensed pressure value $D_{PRE}$ (Step S72). In Step S72, the calibration parameters used in the temperature calibration operation are obtained by using the embodiment shown in FIG. 4A or FIGS. 4B-1~4B-2. In detail, in the situation where only the humidity sensor 10C operates for detecting the environmental humidity (that is, only the first heater 101C is driven), the pressure calculation circuit 111B accesses the memory 115 and uses the look-up table to obtain the first output offset calibration parameter OC1 and the first output gain calibration parameter GC1 corresponding to the second sensed temperature value $T_{h1}$. The pressure calculation circuit 111B generates a control signal S111B according to the first offset calibration parameter OC1 and the first output gain calibration parameter GC1 and provides the control signal S111B to the pressure calibration circuit 112B, so as to perform the temperature calibration operation by controlling the analog front-end circuit 120 (the temperature calibration operation is referred to the previous description). In the situation where the humidity sensor 10C and the gas sensor 10D operate together for sensing the environmental humidity and gas concentration at the same time, (that is, the first and second heaters 101C and 101D are driven at the same time), the pressure calculation circuit 111B accesses the memory 115 and uses the look-up table to obtain the second output offset calibration parameter OC2 and the second output gain calibration parameter GC2 corresponding to the third sensed temperature value $T_{h2}$. The pressure calculation circuit 111B generates the control signal S111B according to the second output offset calibration parameter OC2 and the second output gain calibration parameter GC2 and provides the control signal S111B to the pressure calibration circuit 112B. The pressure calibration circuit 112B generates a calibration signal S112B according to the control signal S111B, and, thus, the temperature calibration operation is performed through the analog front-end circuit 120.

After obtaining the sensed pressure value $D_{PRE}$ generated in response to the temperature calibration operation, the humidity sensor 10C senses the relative humidity of the environment and generates the relative humidity value $D_{HUMD}$ through the operations of the humidity reading circuit 110C and the humidity calculation circuit 111C; and the humidity calculation circuit 111C accesses the memory 115, uses the look-up table, and further performs a calculation using the relative humidity value $D_{HUMD}$, the sensed temperature value $D_{TEMP}$, and the calibrated pressure value $D'_{PRE}$ generated in response to the temperature calibration operation to calibrate the relative humidity value $D_{HUMD}$ and obtain the calibrated humidity value $D'_{HUMD}$ (Step S73). In the situation where only the relative humidity of the environment is sensed, the method terminates after Step S73. In the situation where the gas concentration is further sensed, Step S74 is performed after Step S73. In Step S74, when the gas sensor 10D senses the gas concentration, the gas-concentration reading circuit 110D and the gas-concentration calculation circuit 111D operate to generate a gas-concentration value $D_{GAS}$. Moreover, in Step S74 the baseline resistance value of the gas sensor 10D is compensated for according to the sensed temperature value $D_{TEMP}$, the calibrated pressure value $D'_{PRE}$, and the calibrated humidity value $D'_{HUMD}$. Then, the algorithm of the gas concentration is performed according to the above data to obtain a calibrated gas-concentration value $D'_{GAS}$. Finally, the sensing and calibration operation terminates (Step S75).

According to the foregoing embodiments, the sensing device 1 of the present disclosure integrates the temperature sensor 10A, the pressure sensor 10B, and at least one of the humidity sensor 10C and the gas sensor 10D into a single chip. When only the first heater 101C of the humidity sensor 10C is driven, the sensing device 1 of the present disclosure obtains the temperature calibration parameters of the pressure sensor 10B. When the first heater 101C of the humidity sensor 10C and the second heater 101D of the gas sensor 10D are driven simultaneously, another set of temperature calibration parameters of the pressure sensor 10B is obtained. Therefore, when at least one of the first and/or second heaters 101C and/or 101D is driven, the temperature calibration operation can be performed according to the temperature calibration parameter(s) for pressure sensing, thereby eliminating the thermal interference of the first or second heater 101C or 101D on the pressure sensing and obtaining a more accurate pressure value. After obtaining the calibrated pressure value after the temperature calibration operation, the relative humidity value and the gas-concentration value can be sequentially calibrated according to the calibrated pressure value, so that the calibrated values can accurately reflect the relative humidity and gas concentration of the environment. The temperature calibration parameters in the embodiment are obtained by directly using the first heater 101C of the humidity sensor 10C and/or the second heater 101D of the gas sensor 10D without using additional heaters, which effectively reduces the cost.

In the methods for generating the calibration parameters of the temperature calibration operation shown in FIGS. 4A-4B-1, 4B-2, Step S32 is performed to obtain the second sensed temperature value $T_{h1}$ and the second pressure output value $P_{h10}$ while the first heater 101C is driven. Step S32' shown in FIG. 4B-1 is performed to obtain the third sensed temperature value $T_{h2}$ and the fifth pressure output value $P_{h20}$ while the first heater 101C and the second heater 101D are driven simultaneously.

In another embodiment, Step S32 and Step S32' may be a single heater; that is, the sensing device comprises only one of the first and second heaters 101C and 101D, as described below. In step S31, the first or second heater 101C or 101D is driven to output the first power (i.e., to generate the thermal energy of the first intensity) for obtaining the second sensed temperature value $T_{h1}$ and the second pressure output value $P_{h10}$. In Step S31', the first or second heater 101C and 101D is driven by another voltage to output the second power (i.e., to generate the thermal energy of the second intensity) for obtaining the third sensed temperature value $T_{h2}$ and the fifth pressure output value $P_{h20}$. For example, in the embodiment of FIG. 1C, when Step S31 is performed, the first heater 101C is driven by a voltage for obtaining the second sensed temperature value $T_{h1}$ and the second pressure output value $P_{h10}$; when Step S31' is performed, the first heater 101C is driven by another voltage for obtaining the third sensed temperature value $T_{h2}$ and the fifth pressure output value $P_{h20}$. The heating control circuit of the present disclosure is controlled and driven by a signal sent from the pressure calculation circuit and then further drives the first heater or the second heater.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A sensing device comprising:
   a processing circuit; and
   a multi-sensor integrated single chip electrically connected to the processing circuit and comprising:
     a substrate;
     a temperature sensor disposed on the substrate and configured to sense temperature;
     a pressure sensor disposed on the substrate and configured to sense pressure; and
     a first environmental sensor disposed on the substrate and configured to sense a first environmental state;
   wherein the processing circuit is configured to:
     establish a look-up table which comprises a relationship between temperature to an output offset calibration parameter and an output gain calibration parameter of the pressure sensor;
     store the look-up table in a memory;
     obtain a first sensed temperature value from the temperature sensor when the first environmental sensor does not operate;
     obtain a second sensed temperature value from the temperature sensor when the first environmental sensor operates;
     obtain a sensed pressure value from the pressure sensor; and
     access the memory to obtain the output offset calibration parameter and the output gain calibration parameter of the pressure sensor from the look-up table according to the first sensed temperature value and the second sensed temperature value and calibrate the sensed pressure value according to the output offset calibration parameter and the output gain calibration parameter to generate a calibrated pressure value.

2. The sensing device as claimed in claim 1, wherein the first environmental sensor comprises a first sensing element and a first heater, the first heater can generate thermal energy to raise the temperature of the first sensing element and the substrate, and the temperature sensor senses the temperature of the substrate.

3. The sensing device as claimed in claim 1, wherein the first environmental sensor is a humidity sensor or a gas sensor, and the first environmental state is relative humidity or gas concentration.

4. The sensing device as claimed in claim 1, wherein the processing circuit is further configured to:
   obtain a sensed first environmental state value from the first environmental sensor; and
   perform a calculation using the calibrated pressure value and the second sensed temperature value to calibrate the sensed first environmental state value and generate a calibrated first environmental state value.

5. The sensing device as claimed in claim 4, wherein the first environmental sensor is a humidity sensor, the first environmental state is relative humidity, and the sensed first environmental state value and the calibrated first environmental state value are relative humidity values.

6. The sensing device as claimed in claim 1, wherein the at least one temperature calibration parameter comprises a first output offset calibration parameter.

7. The sensing device as claimed in claim 1, wherein the at least one temperature calibration parameter comprises a first output gain calibration parameter.

8. The sensing device as claimed in claim 1, wherein the multi-sensor integrated single chip further comprises a second environmental sensor disposed on the substrate, the second environmental sensor is configured to sense a second environmental state, and the processing circuit is further configured to:
   obtain a sensed first environmental state value from the first environmental sensor and perform a calculation using the calibrated pressure value and the second sensed temperature value to calibrate the sensed first environmental state value and generate a calibrated first environmental state value; and
   obtain a sensed second environmental state value from the second environmental sensor and perform a calculation using the calibrated first environmental state value to calibrate the sensed second environmental state value and generate a calibrated second environmental state value.

9. The sensing device as claimed in claim 8, wherein:
   the first environmental sensor is a humidity sensor, the first environmental state is relative humidity, and the sensed first environmental state value and the calibrated first environmental state value are relative humidity values,
   the second environmental sensor is a gas sensor, the second environmental state is gas concentration, and the sensed second environmental state value and the calibrated second environmental state value are gas-concentration values, and
   the processing circuit is further configured to:
     perform a calculation using the second sensed temperature value and the calibrated first environmental state value to compensate for a baseline resistance value of the second environmental sensor; and
     perform a calculation using the compensated baseline resistance value to calibrate the sensed second environmental state value and generate the calibrated second environmental state value.

10. The sensing device as claimed in claim 8, wherein the first environmental sensor comprises a first sensing element and a first heater, the second environmental sensor comprises a second sensing element, and the processing circuit is further configured to:
    drive the first heater to output first power; and
    drive the first heater to output second power,
    wherein the first heater raises the temperature of the substrate, the temperature of the first sensing element, and the temperature of the second sensing element,
    wherein when the first heater outputs the first power, the temperature sensor operates, and the first sensed temperature value is obtained, and wherein when the first heater outputs the second power, the temperature sensor operates, and the second sensed temperature value is obtained.

11. The sensing device as claimed in claim 8, wherein:
the first environmental sensor comprises a first sensing element and a first heater, the second environmental sensor comprises a second sensing element and a second heater, and the first heater and the second heater operate to raise the temperature of the substrate, the temperature of the first sensing element, and the temperature of the second sensing element,
when the first heater operates and the second heater dose not operate, the temperature sensor operates to obtain the first sensed temperature value, and
when the first heater and the second heater simultaneously operate, the temperature sensor operates to obtain the second sensed temperature value.

12. A calibration method for a sensing device, the sensing device comprising a multi-sensor integrated single chip and a processing circuit, the multi-sensor integrated single chip comprising a temperature sensor, a pressure sensor, and a first environmental sensor, and the calibration method comprising:
by the processing circuit, establishing a look-up table which comprises a relationship between temperature to an output offset calibration parameter and an output gain calibration parameter of the pressure sensor;
by the processing circuit, storing the look-up table in a memory;
by the processing circuit, driving the temperature sensor to sense temperature and generating a first sensed temperature value;
by the processing circuit, driving the first environmental sensor to operate, and driving the temperature sensor to sense temperature, and generating a second sensed temperature value;
by the processing circuit, driving the pressure sensor to sense pressure and generating a sensed pressure value; and
by the processing circuit, accessing the memory to obtain the output offset calibration parameter and the output gain calibration parameter of the pressure sensor from the look-up table according to the first sensed temperature value and the second sensed temperature value and calibrating the sensed pressure value according to the output offset calibration parameter and the output gain calibration parameter to generate a calibrated pressure value.

13. The calibration method as claimed in claim 12, wherein the first environmental sensor comprises a first sensing element and a first heater, and when the processing circuit drives the first heater to operate, the processing circuit drives the temperature sensor to operate and generates the second sensed temperature value.

14. The calibration method as claimed in claim 12, wherein the first environmental sensor is a humidity sensor or a gas sensor, and the sensed first environmental state value is a relative humidity value or a gas-concentration value.

15. The calibration method as claimed in claim 12, further comprising:
by the processing circuit, driving the first environmental sensor to sense a first environmental state and generating a sensed first environmental state value; and
by the processing circuit, performing a calculation using the calibrated pressure value and the second sensed temperature value to calibrate the sensed first environmental state value and generate a calibrated first environmental state value.

16. The calibration method as claimed in claim 15, wherein the first environmental sensor is a humidity sensor, and the first environmental state is relative humidity, and the sensed first environmental state value and the calibrated first environmental state value are relative humidity values.

17. The calibration method as claimed in claim 12, wherein the step of obtaining the at least one temperature calibration parameter of the pressure sensor according to the first sensed temperature value and the second sensed temperature value by the processing circuit comprises:
by the processing circuit, obtaining a first output offset calibration parameter among the at least one temperature calibration parameter,
wherein the first output offset calibration parameter corresponds to the first sensed temperature value and the second sensed temperature value.

18. The calibration method as claimed in claim 12, wherein the step of obtaining the at least one temperature calibration parameter of the pressure sensor according to the first sensed temperature value and the second sensed temperature value by the processing circuit comprises:
by the processing circuit, obtaining a first output gain calibration parameter among the at least one temperature calibration parameter,
wherein the first output gain calibration parameter corresponds to the first sensed temperature value and the second sensed temperature value.

19. The calibration method as claimed in claim 12, wherein the multi-sensor integrated single chip further comprises a second environmental sensor configured to sense a second environmental state, and the calibration method further comprises:
by the processing circuit, driving the first environmental sensor to operate and obtaining a sensed first environmental state value;
by the processing circuit, performing a calculation using the calibrated pressure value and the second sensed temperature value to calibrate the sensed first environmental state value and generate a calibrated first environmental state value;
by the processing circuit, driving the second environmental sensor to operate and obtaining a sensed second environmental state value; and
by the processing circuit, performing a calculation using the calibrated first environmental state value to calibrate the sensed second environmental state value and generate a calibrated second environmental state value.

20. The calibration method as claimed in claim 19, wherein
the first environmental sensor is a humidity sensor, the first environmental state is relative humidity, and the sensed first environmental state value and the calibrated first environmental state value are relative humidity values,
the second environmental sensor is a gas sensor, the second environmental state is gas concentration, and the sensed second environmental state value and the calibrated second environmental state value are gas-concentration values, and
the step of performing the calculation using the calibrated first environmental state value to calibrate the sensed second environmental state value and generate the calibrated second environmental state value comprises:

by the processing circuit, performing a calculation using the second sensed temperature value and the calibrated first environmental state value to compensate for a baseline resistance value of the second environmental sensor; and by the processing circuit, performing a calculation using the compensated baseline resistance value to calibrate the sensed second environmental state value and generate the calibrated second environmental state value.

21. The calibration method as claimed in claim 19, wherein the second environmental sensor comprises a second sensing element, the first environmental sensor comprises a first sensing element and a first heater, the first heater raises the temperature of the substrate, the temperature of the first sensing element, and the temperature of the second sensing element, and the calibration method further comprises:

by the processing circuit, driving the first heater to output a first power; and by the processing circuit, driving the first heater to output a second power, wherein when the first heater outputs the first power, the temperature sensor operates to obtain the first sensed temperature value, and wherein when the first heater outputs the second power, the temperature sensor operates to obtain the second sensed temperature value.

22. The calibration method as claimed in claim 19, wherein the first environmental sensor comprises a first sensing element and a first heater, and the second environmental sensor comprises a second sensing element and a second heater, the first heater and the second heater raise the temperature of the substrate, the temperature of the first sensing element, and the temperature of the second sensing element to rise, and the calibration method further comprises:

by the processing circuit, driving the first heater to operate; and by the processing circuit, driving the first heater and the second heater to operate simultaneously, wherein when the first heater operates and the second heater dose not operate, the temperature sensor operates to obtain the first sensed temperature value, and wherein when the first heater and the second heater operate at the same time, the temperature sensor operates to obtain the second sensed temperature value.

23. The calibration method as claimed in claim 19, wherein, the step of obtaining the at least one temperature calibration parameter of the pressure sensor according to the first sensed temperature value and the second sensed temperature value by the processing circuit comprises:

applying a first atmospheric pressure to the sensing device;

when the first atmospheric pressure is applied to the sensing device and the temperature sensor operates and obtains the first sensed temperature value, driving the pressure detector to sense pressure and generating a first pressure output value by the processing circuit;

when the first atmospheric pressure is applied to the sensing device and the temperature sensor operates and obtains the second sensed temperature value, driving the pressure detector to sense pressure and generating a second pressure output value by the processing circuit; and by the processing circuit, performing a calculation using the first sensed temperature value, the second sensed temperature value, the first pressure output value, and the second pressure output value to obtain a first output offset calibration parameter among the at least one temperature calibration parameters.

24. The calibration method as claimed in claim 23, wherein the step of obtaining the at least one temperature calibration parameter of the pressure sensor according to the first sensed temperature value and the second sensed temperature value by the processing circuit further comprises:

applying a second atmospheric pressure to the sensing device;

when the sensing device is applied by the second atmospheric pressure and the temperature sensor operates and obtains the first sensed temperature value, driving the pressure detector to detect pressure and generating a third pressure output value by the processing circuit;

when the second atmospheric pressure is applied to the sensing device and the temperature sensor operates and obtains the second sensed temperature value, driving the pressure detector to detect pressure and generating a fourth pressure output value by the processing circuit; and by the processing circuit, performing a calculation using the first sensed temperature value, the second sensed temperature value, the first pressure output value, the second pressure output value, the third pressure output value, and the fourth pressure output value to obtain a first output gain calibration parameter among the at least one temperature calibration parameter.

* * * * *